(12) United States Patent
Yang et al.

(10) Patent No.: US 11,781,132 B2
(45) Date of Patent: Oct. 10, 2023

(54) DNA EXTRACTION METHOD USING MICROWAVE FOR NEXT GENERATION SEQUENCING AND USE THEREOF

(71) Applicants: MACROGEN, INC., Seoul (KR); PSOMAGEN, INC., Rockville, MD (US)

(72) Inventors: Joshua Sungwoo Yang, Bucheon-si (KR); Jaekyung Chon, Seoul (KR); Ik Jung Choi, Seoul (KR); Hyun Min Park, Seoul (KR); Jieun Park, Seoul (KR); Jeongsun Seo, Seoul (KR); Changhoon Kim, Gwangmyeong-si (KR); Jong Yeon Shin, Gwangmyeong-si (KR); Han Sol Seo, Yongin-si (KR); Jiwon Shin, Gunpo-si (KR); In Hee Hwang, Seoul (KR); Seon Hye Sim, Seoul (KR); Chang Woo Cho, Anyang-si (KR); Kyuin Hwang, Incheon (KR); In Seon Kim, Bucheon-si (KR); Hyung Il Lee, Seoul (KR); Jung Hyun Cho, Gwangmyeong-si (KR)

(73) Assignees: MACROGEN, INC., Seoul (KR); PSOMAGEN, INC., Rockville, MD (US)

( * ) Notice: Subject to any disclaimer, the term of this patent is extended or adjusted under 35 U.S.C. 154(b) by 106 days.

(21) Appl. No.: 16/830,565

(22) Filed: Mar. 26, 2020

(65) Prior Publication Data
US 2021/0130812 A1    May 6, 2021

(30) Foreign Application Priority Data
Nov. 5, 2019    (KR) .................... 10-2019-0140300

(51) Int. Cl.
*C12N 15/10*    (2006.01)
*C12Q 1/6806*    (2018.01)
*C12Q 1/6844*    (2018.01)

(52) U.S. Cl.
CPC ..... *C12N 15/1082* (2013.01); *C12N 15/1003* (2013.01); *C12Q 1/6806* (2013.01); *C12Q 1/6844* (2013.01)

(58) Field of Classification Search
CPC ............ C12N 15/1082; C12N 15/1003; C12Q 1/6844; C12Q 1/6806
See application file for complete search history.

(56) References Cited

U.S. PATENT DOCUMENTS

| | | | |
|---|---|---|---|
| 5,612,473 A | * | 3/1997 | Wu et al. .................... 536/25.42 |
| 10,456,769 B2 | * | 10/2019 | Wang et al. ......... B01J 19/0046 |
| 2016/0312174 A1 | * | 10/2016 | Geddes et al. ......... C12M 47/06 |
| 2018/0195111 A1 | * | 7/2018 | Gosiewski et al. .... C12Q 1/689 |

FOREIGN PATENT DOCUMENTS

| | | | |
|---|---|---|---|
| KR | 10-1651817 B1 | 8/2016 | |
| WO | WO 2017/192974 A1 * | 11/2017 | ............... C12Q 1/68 |
| WO | WO 2017/222164 A1 * | 12/2017 | ............... C12Q 1/68 |

OTHER PUBLICATIONS

Picard et al. "Detection and Enumeration of Bacteria in Soil by Direct DNA Extraction and Polymerase Chain Reaction" Applied and Environmental Microbiology, Sep. 1992, 58(9):2717-2722 (Year: 1992).*

Rasmussen et al. "Rapid preparation of cyanobacterial DNA for real-time PCR analysis" Letters in Applied Microbiology (2008) 46: 14-19 (Year: 2008).*

Yang et al. "Fragmentation of genomic DNA using microwave irradiation." Journal of Biomolecular Techniques vol. 24, 2 (2013): 98-103; doi:10.7171/jbt.13-2402-005 (Year: 2013).*

Bastian Dörnte et al., "Fast Microwave-based DNA Extraction from Vegetative Mycelium and Fruiting Body Tissues of Agaricomycetes for PCR Amplification", Current Trends in Biotechnology and Pharmacy, Oct. 2013, pp. 825-836, vol. 7, No. 4.

* cited by examiner

*Primary Examiner* — Kaijiang Zhang
(74) *Attorney, Agent, or Firm* — Paratus Law Group, PLLC

(57) ABSTRACT

Disclosed are a method for DNA extraction in a sample for next generation sequencing (NGS) and a method of constructing a NGS library using the extracted DNA. The method for DNA extraction includes: preparing a mixture by mixing a biological sample with a buffer; applying microwaves to the mixture; and recovering DNA. The method of constructing a NGS library includes: extracting DNA according to the method for DNA extraction; amplifying a target DNA using primers; and purifying the amplified product and subjecting the purified product to library pooling.

6 Claims, 23 Drawing Sheets

Specification includes a Sequence Listing.

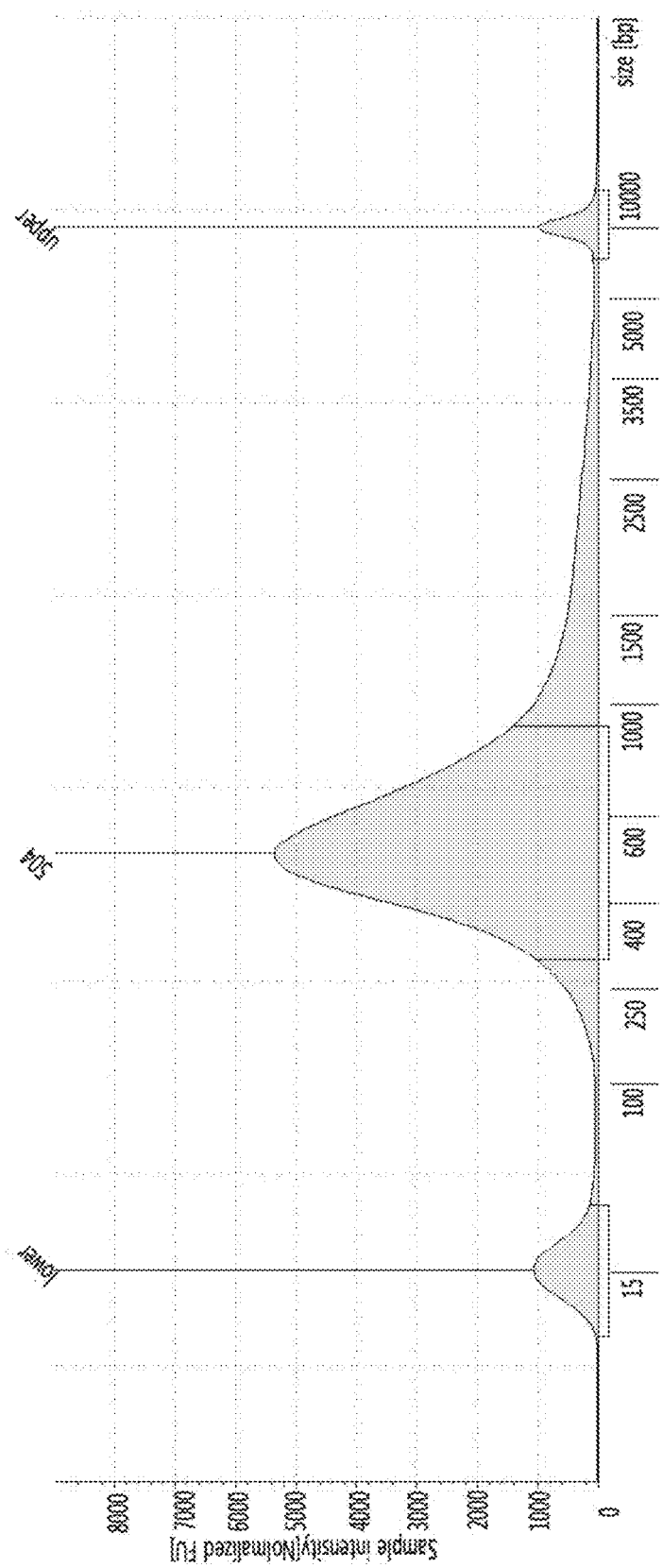

SEQUENCE LISTING

<160> NUMBER OF SEQ ID NOS: 33

<210> SEQ ID NO 1
<211> LENGTH: 87
<212> TYPE: DNA
<213> ORGANISM: Artificial Sequence
<220> FEATURE:
<223> OTHER INFORMATION: Primer (MS_502)

<400> SEQUENCE: 1
aatgatacgg cgaccaccga gatctacacc tctctattcg tcggcagcgt cagatgtgta    60
taagagacag cctacgggag gcagcag    87

-continued

```
<210> SEQ ID NO 2
<211> LENGTH: 87
<212> TYPE: DNA
<213> ORGANISM: Artificial Sequence
<220> FEATURE:
<223> OTHER INFORMATION: Primer (MS_503)

<400> SEQUENCE: 2
aatgatacgg cgaccaccga gatctacact atcctcttcg tcggcagcgt cagatgtgta      60
taagagacag cctacgggag gcagcag                                         87

<210> SEQ ID NO 3
<211> LENGTH: 87
<212> TYPE: DNA
<213> ORGANISM: Artificial Sequence
<220> FEATURE:
<223> OTHER INFORMATION: Primer (MS_505)

<400> SEQUENCE: 3
aatgatacgg cgaccaccga gatctacacg taaggagtcg tcggcagcgt cagatgtgta      60
taagagacag cctacgggag gcagcag                                         87

<210> SEQ ID NO 4
<211> LENGTH: 87
<212> TYPE: DNA
<213> ORGANISM: Artificial Sequence
<220> FEATURE:
<223> OTHER INFORMATION: Primer (MS_513)

<400> SEQUENCE: 4
aatgatacgg cgaccaccga gatctacact cgactagtcg tcggcagcgt cagatgtgta      60
taagagacag cctacgggag gcagcag                                         87

<210> SEQ ID NO 5
<211> LENGTH: 87
<212> TYPE: DNA
<213> ORGANISM: Artificial Sequence
<220> FEATURE:
<223> OTHER INFORMATION: Primer (MS_515)

<400> SEQUENCE: 5
aatgatacgg cgaccaccga gatctacact tctagcttcg tcggcagcgt cagatgtgta      60
taagagacag cctacgggag gcagcag                                         87

<210> SEQ ID NO 6
<211> LENGTH: 87
<212> TYPE: DNA
<213> ORGANISM: Artificial Sequence
<220> FEATURE:
<223> OTHER INFORMATION: Primer (MN_701)

<400> SEQUENCE: 6
caagcagaag acggcatacg agattcgcct tagtctcgtg ggctcggaga tgtgtataag      60
agacaggact achvgggtat ctaatcc                                         87

<210> SEQ ID NO 7
<211> LENGTH: 87
<212> TYPE: DNA
<213> ORGANISM: Artificial Sequence
<220> FEATURE:
<223> OTHER INFORMATION: Primer (MN_702)

<400> SEQUENCE: 7
```
caagcagaag acggcatacg agatctagta cggtctcgtg ggctcggaga tgtgtataag    60
agacaggact achvgggtat ctaatcc                                        87

<210> SEQ ID NO 8
<211> LENGTH: 87
<212> TYPE: DNA
<213> ORGANISM: Artificial Sequence
<220> FEATURE:
<223> OTHER INFORMATION: Primer (MN_703)

<400> SEQUENCE: 8
caagcagaag acggcatacg agatttctgc ctgtctcgtg ggctcggaga tgtgtataag    60
agacaggact achvgggtat ctaatcc                                        87

<210> SEQ ID NO 9
<211> LENGTH: 87
<212> TYPE: DNA
<213> ORGANISM: Artificial Sequence
<220> FEATURE:
<223> OTHER INFORMATION: Primer (MN_704)

<400> SEQUENCE: 9
caagcagaag acggcatacg agatgctcag gagtctcgtg ggctcggaga tgtgtataag    60
agacaggact achvgggtat ctaatcc                                        87

<210> SEQ ID NO 10
<211> LENGTH: 87
<212> TYPE: DNA
<213> ORGANISM: Artificial Sequence
<220> FEATURE:
<223> OTHER INFORMATION: Primer (MN_705)

<400> SEQUENCE: 10
caagcagaag acggcatacg agataggagt ccgtctcgtg ggctcggaga tgtgtataag    60
agacaggact achvgggtat ctaatcc                                        87

<210> SEQ ID NO 11
<211> LENGTH: 87
<212> TYPE: DNA
<213> ORGANISM: Artificial Sequence
<220> FEATURE:
<223> OTHER INFORMATION: Primer (MN_706)

<400> SEQUENCE: 11
caagcagaag acggcatacg agatcatgcc tagtctcgtg ggctcggaga tgtgtataag    60
agacaggact achvgggtat ctaatcc                                        87

<210> SEQ ID NO 12
<211> LENGTH: 87
<212> TYPE: DNA
<213> ORGANISM: Artificial Sequence
<220> FEATURE:
<223> OTHER INFORMATION: Primer (MN_707)

<400> SEQUENCE: 12
caagcagaag acggcatacg agatgtagag aggtctcgtg ggctcggaga tgtgtataag    60
agacaggact achvgggtat ctaatcc                                        87

<210> SEQ ID NO 13
<211> LENGTH: 87
<212> TYPE: DNA
<213> ORGANISM: Artificial Sequence

```
<220> FEATURE:
<223> OTHER INFORMATION: Primer (MN_708)

<400> SEQUENCE: 13
caagcagaag acggcatacg agatcctctc tggtctcgtg ggctcggaga tgtgtataag    60
agacaggact achvgggtat ctaatcc                                        87

<210> SEQ ID NO 14
<211> LENGTH: 87
<212> TYPE: DNA
<213> ORGANISM: Artificial Sequence
<220> FEATURE:
<223> OTHER INFORMATION: Primer (MN_709)

<400> SEQUENCE: 14
caagcagaag acggcatacg agatagcgta gcgtctcgtg ggctcggaga tgtgtataag    60
agacaggact achvgggtat ctaatcc                                        87

<210> SEQ ID NO 15
<211> LENGTH: 87
<212> TYPE: DNA
<213> ORGANISM: Artificial Sequence
<220> FEATURE:
<223> OTHER INFORMATION: Primer (MN_710)

<400> SEQUENCE: 15
caagcagaag acggcatacg agatcagcct cggtctcgtg ggctcggaga tgtgtataag    60
agacaggact achvgggtat ctaatcc                                        87

<210> SEQ ID NO 16
<211> LENGTH: 17
<212> TYPE: DNA
<213> ORGANISM: Artificial Sequence
<220> FEATURE:
<223> OTHER INFORMATION: Primer (341F)

<400> SEQUENCE: 16
cctacgggag gcagcag                                                   17

<210> SEQ ID NO 17
<211> LENGTH: 21
<212> TYPE: DNA
<213> ORGANISM: Artificial Sequence
<220> FEATURE:
<223> OTHER INFORMATION: Primer (R805)

<400> SEQUENCE: 17
gactachvgg gtatctaatc c                                              21

<210> SEQ ID NO 18
<211> LENGTH: 20
<212> TYPE: DNA
<213> ORGANISM: Artificial Sequence
<220> FEATURE:
<223> OTHER INFORMATION: Primer (Firm_F)

<400> SEQUENCE: 18
ctgatggagc aacgccgcgt                                                20

<210> SEQ ID NO 19
<211> LENGTH: 20
<212> TYPE: DNA
<213> ORGANISM: Artificial Sequence
<220> FEATURE:
```

```
<223> OTHER INFORMATION: Primer (Firm_R)

<400> SEQUENCE: 19
acacytagya ctcatcgttt                                                    20

<210> SEQ ID NO 20
<211> LENGTH: 23
<212> TYPE: DNA
<213> ORGANISM: Artificial Sequence
<220> FEATURE:
<223> OTHER INFORMATION: Primer (Bact_F)

<400> SEQUENCE: 20
ccggawtyat tgggtttaaa ggg                                                23

<210> SEQ ID NO 21
<211> LENGTH: 18
<212> TYPE: DNA
<213> ORGANISM: Artificial Sequence
<220> FEATURE:
<223> OTHER INFORMATION: Primer (Bact_R)

<400> SEQUENCE: 21
ggtaaggttc ctcgcgta                                                      18

<210> SEQ ID NO 22
<211> LENGTH: 18
<212> TYPE: DNA
<213> ORGANISM: Artificial Sequence
<220> FEATURE:
<223> OTHER INFORMATION: Primer (Acti_F)

<400> SEQUENCE: 22
gcgkcctatc agcttgtt                                                      18

<210> SEQ ID NO 23
<211> LENGTH: 21
<212> TYPE: DNA
<213> ORGANISM: Artificial Sequence
<220> FEATURE:
<223> OTHER INFORMATION: Primer (Acti_R)

<400> SEQUENCE: 23
ccgcctacga gcyctttacg c                                                  21

<210> SEQ ID NO 24
<211> LENGTH: 20
<212> TYPE: DNA
<213> ORGANISM: Artificial Sequence
<220> FEATURE:
<223> OTHER INFORMATION: Primer (Pro_F)

<400> SEQUENCE: 24
tggtgtaggg gtaaaatccg                                                    20

<210> SEQ ID NO 25
<211> LENGTH: 21
<212> TYPE: DNA
<213> ORGANISM: Artificial Sequence
<220> FEATURE:
<223> OTHER INFORMATION: Primer (Pro_R)

<400> SEQUENCE: 25
aggtaaggtt cttcgygtat c                                                  21
```

<210> SEQ ID NO 26
<211> LENGTH: 17
<212> TYPE: DNA
<213> ORGANISM: Artificial Sequence
<220> FEATURE:
<223> OTHER INFORMATION: Primer (Bifi_F)

<400> SEQUENCE: 26
ctcctggaaa cgggtgg                                                  17

<210> SEQ ID NO 27
<211> LENGTH: 17
<212> TYPE: DNA
<213> ORGANISM: Artificial Sequence
<220> FEATURE:
<223> OTHER INFORMATION: Primer (Bifi_R)

<400> SEQUENCE: 27
ctttcacacc rgacgcg                                                  17

<210> SEQ ID NO 28
<211> LENGTH: 18
<212> TYPE: DNA
<213> ORGANISM: Artificial Sequence
<220> FEATURE:
<223> OTHER INFORMATION: Primer (Ente_F)

<400> SEQUENCE: 28
cgtcgcaagm mcaaagag                                                 18

<210> SEQ ID NO 29
<211> LENGTH: 19
<212> TYPE: DNA
<213> ORGANISM: Artificial Sequence
<220> FEATURE:
<223> OTHER INFORMATION: Primer (Ente_R)

<400> SEQUENCE: 29
ttaccgcggc tgctggcac                                                19

<210> SEQ ID NO 30
<211> LENGTH: 22
<212> TYPE: DNA
<213> ORGANISM: Artificial Sequence
<220> FEATURE:
<223> OTHER INFORMATION: Primer (Clos_F)

<400> SEQUENCE: 30
aaaggaagat taataccgca ta                                            22

<210> SEQ ID NO 31
<211> LENGTH: 20
<212> TYPE: DNA
<213> ORGANISM: Artificial Sequence
<220> FEATURE:
<223> OTHER INFORMATION: Primer (Clos_R)

<400> SEQUENCE: 31
ttcttcctaa tctctacgca                                               20

<210> SEQ ID NO 32
<211> LENGTH: 19
<212> TYPE: DNA
<213> ORGANISM: Artificial Sequence
<220> FEATURE:
<223> OTHER INFORMATION: Primer (Baci_F)

```
<400> SEQUENCE: 32
gcagtaggga atcttccgc                                              19

<210> SEQ ID NO 33
<211> LENGTH: 20
<212> TYPE: DNA
<213> ORGANISM: Artificial Sequence
<220> FEATURE:
<223> OTHER INFORMATION: Primer (Baci_R)

<400> SEQUENCE: 33
acacttagca ctcatcgttt                                             20
```

DNA EXTRACTION METHOD USING MICROWAVE FOR NEXT GENERATION SEQUENCING AND USE THEREOF

CROSS-REFERENCE TO RELATED APPLICATION

This application claims priority to and the benefit of Korean Patent Application No. 10-2019-0140300, filed on Nov. 5, 2019, the disclosure of which is incorporated herein by reference in its entirety.

BACKGROUND

1. Field

The present disclosure relates to a method for DNA extraction in a biological sample for next generation sequencing and a use thereof, and more particularly to a DNA extraction method for constructing a library for next generation sequencing (NGS) by using microwaves, and a method of constructing a NGS library using the extracted DNA.

2. Description of Related Art

Next-generation sequencing is a high-speed method of analyzing genome sequences and is also called high-throughput sequencing, massively parallel sequencing, or second-generation sequencing. Unlike the existing Sanger's sequencing method, this method is characterized by processing a large number of (more than one million) DNA fragments in parallel. With the advent of next-generation sequencing, the cost required for genome analysis is dramatically lowered and is being used in various fields.

Next generation sequencing (NGS) technology enables analysis of the entire genome across DNA levels, transcripts (RNA levels), and epigenetic levels, and to this end, includes various analysis platforms such as whole genome sequencing (WGS), whole exome sequencing (WES), and whole transcriptome sequencing (WTS).

Meanwhile, to perform NGS, DNA should be extracted from a biological sample, which takes a lot of time and money in the DNA extraction process. To address this problem, various studies are ongoing (Korean Patent Publication No. 10-1651817), but a commercially available kit based on a cell lysis method using physical DNA extraction (bead beating, nitrogen decompression, sonication, homogenization, or the like) or chemical DNA extraction (detergent, enzyme, solvent, surfactant, or the like) is still most widely used. Therefore, there is an urgent need to develop a method capable of more simply extracting DNA other than the above-described methods.

SUMMARY

As a result of having conducted intensive studies on whether DNA extracted by applying microwaves to a biological sample is applicable to next generation sequencing, the inventors of the present disclosure confirmed that it is possible to construct a 16s rRNA library and a library for WMS using the extracted DNA and first verified the possibility of next generation sequencing using the sample, and thus completed the present disclosure based on these findings.

Provided is a method for DNA extraction in a biological sample for next generation analysis (NGS), the method including the following processes:
(1) preparing a mixture by mixing a biological sample with a buffer;
(2) applying microwaves to the mixture; and
(3) recovering DNA.

Provided is a method of constructing a next generation sequencing (NGS) library, including the following processes:
(a) extracting DNA according to the DNA extraction method;
(b) amplifying a target DNA using primers; and
(c) purifying the amplified product and subjecting the purified product to library pooling.

Additional aspects will be set forth in part in the description which follows and, in part, will be apparent from the description, or may be learned by practice of the presented embodiments.

According to an aspect of the present disclosure, there is provided a method for DNA extraction in a biological sample for next generation analysis (NGS), the method including the following processes:
(1) preparing a mixture by mixing a biological sample with a buffer;
(2) applying microwaves to the mixture; and
(3) recovering DNA.

In one embodiment of the present disclosure, process (3) may be a DNA extraction method including the following processes:
(3-1) centrifuging the resulting mixture obtained in process (2); and
(3-2) separating a supernatant from the centrifuged mixture obtained in process (3-1).

In another embodiment of the present disclosure, the mixture of process (1) may have a volume of about 20% to about 32% with respect to that of a container (tube).

In another embodiment of the present disclosure, the mixture of process (1) may have a concentration of about 200 g/L to about 300 g/L.

In another embodiment of the present disclosure, the buffer of process (1) may be a Tris-EDTA (TE) buffer.

In another embodiment of the present disclosure, process (2) may be repeatedly performed.

In another embodiment of the present disclosure, the microwaves of process (2) may be applied for about 30 seconds to about 90 seconds.

According to another aspect of the present disclosure, there is provided a method of constructing a next generation sequencing (NGS) library, the method including the following processes:
a) extracting DNA according to the DNA extraction method;
b) amplifying a target DNA using primers; and
c) purifying the amplified product and subjecting the purified product to library pooling.

In one embodiment of the present disclosure, the primers of process b) may be at least one primer pair selected from the group consisting of:
a primer consisting of a nucleotide sequence represented by SEQ ID NO: 1;
a primer consisting of a nucleotide sequence represented by SEQ ID NO: 2;
a primer consisting of a nucleotide sequence represented by SEQ ID NO: 3;
a primer consisting of a nucleotide sequence represented by SEQ ID NO: 4;

a primer consisting of a nucleotide sequence represented by SEQ ID NO: 5;
a primer consisting of a nucleotide sequence represented by SEQ ID NO: 6;
a primer consisting of a nucleotide sequence represented by SEQ ID NO: 7;
a primer consisting of a nucleotide sequence represented by SEQ ID NO: 8;
a primer consisting of a nucleotide sequence represented by SEQ ID NO: 9;
a primer consisting of a nucleotide sequence represented by SEQ ID NO: 10;
a primer consisting of a nucleotide sequence represented by SEQ ID NO: 11;
a primer consisting of a nucleotide sequence represented by SEQ ID NO: 12;
a primer consisting of a nucleotide sequence represented by SEQ ID NO: 13;
a primer consisting of a nucleotide sequence represented by SEQ ID NO: 14; and
a primer consisting of a nucleotide sequence represented by SEQ ID NO: 15.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which:

FIGS. 1A and 1B illustrate the results of confirming that DNA extracted by applying microwaves and a library constructed using a commercial kit (Illumina NEXTERA XT) represent intestinal microflora, wherein FIG. 1A illustrates PCR conditions used to amplify the extracted DNA, and FIG. 1B illustrates electrophoresis results of the amplified product;

FIGS. 2A-2C illustrate the results of confirming the possibility of constructing a 16s rRNA library using DNA extracted by applying microwaves and a commercial kit (Illumina NEXTERA), wherein FIG. 2A illustrates the results of measuring the size and concentration of a 16s RNA library constructed using the extracted DNA and the commercial kit, FIG. 2B illustrates the results of measuring the size and concentration of another 16s rRNA library constructed using the extracted DNA and the commercial kit, and FIG. 2C illustrates the results of measuring the size and concentration of another 16s rRNA library constructed using the extracted DNA and the commercial kit;

FIGS. 3A and 3B illustrate the results of confirming that DNA extracted by applying microwaves and a library constructed using merged primers according to the present disclosure represent intestinal microflora, wherein FIG. 3A illustrates PCR conditions used to amplify the extracted DNA, and FIG. 3B illustrates electrophoresis results of the amplified product;

FIGS. 4A-4C illustrate the results of confirming the possibility of constructing a 16s rRNA library using DNA extracted by applying microwaves and merged primers according to the present disclosure, wherein FIG. 4A illustrates the results of measuring the size and concentration of a 16s rRNA library constructed using the extracted DNA and primers of SEQ ID NOS: 1 and 6, FIG. 4B illustrates the results of measuring the size and concentration of another 16s rRNA library constructed using the extracted DNA and primers of SEQ ID NOS: 2 and 7, and FIG. 4C illustrates the results of measuring the size and concentration of another 16s rRNA library constructed using the extracted DNA and primers of SEQ ID NOS: 3 and 8;

FIGS. 5A and 5B illustrate the results of confirming the possibility of constructing libraries for WMS using DNA extracted by applying microwaves and commercial kits (Illumina NEXTERA XT or Illumina NEXTERA DNA Flex), wherein FIG. 5A illustrates the results of measuring the size, DNA concentration, and DNA molar concentration of a library for WMS constructed using the extracted DNA and the commercial kit (Illumina NEXTERA XT), and FIG. 5B illustrates the results of measuring the size, DNA concentration, and DNA molar concentration of a library for WMS constructed using the extracted DNA and the commercial kit (Illumina NEXTERA DNA Flex);

FIGS. 7A-7C illustrate quantification results of a library through qRT-PCR, wherein FIG. 7A illustrates the number of raw reads, FIG. 7B illustrates the number of QC passed reads, and FIG. 7C illustrates a ratio of QC passed reads to raw reads;

FIGS. 8A-8D illustrate results of genetic diversity for each biological sample and experimental group, wherein FIG. 8A illustrates the number of QC passed read-based ASVs, FIG. 8B illustrates QC passed read-based Shannon values, FIG. 8C illustrates the number of ASVs based on 10,000 reads, and FIG. 8D illustrates Shannon values based on 10,000 reads;

FIGS. 9A and 9B illustrate the results of confirming the distribution of microflora according to experimental group using a Canine (female, 8 months old)-derived sample, wherein FIG. 9A illustrates the results of confirming the distribution of microflora at a class level, and FIG. 9B illustrates the results of confirming the distribution of microflora at a genus level;

FIGS. 10A and 10B illustrate the results of confirming the distribution of microflora according to experimental group using a human (female, 20 months old)-derived sample, wherein FIG. 10A illustrates the results of confirming the distribution of microflora at a class level, and FIG. 10B illustrates the results of confirming the distribution of microflora at a genus level;

FIGS. 11A and 11B illustrate the results of confirming the distribution of microflora according to experimental group using a human (female, 30 months old)-derived sample, wherein FIG. 11A illustrates the results of confirming the distribution of microflora at a class level, and FIG. 11B illustrates the results of confirming the distribution of microflora at a genus level.

DETAILED DESCRIPTION

Figure 1A:
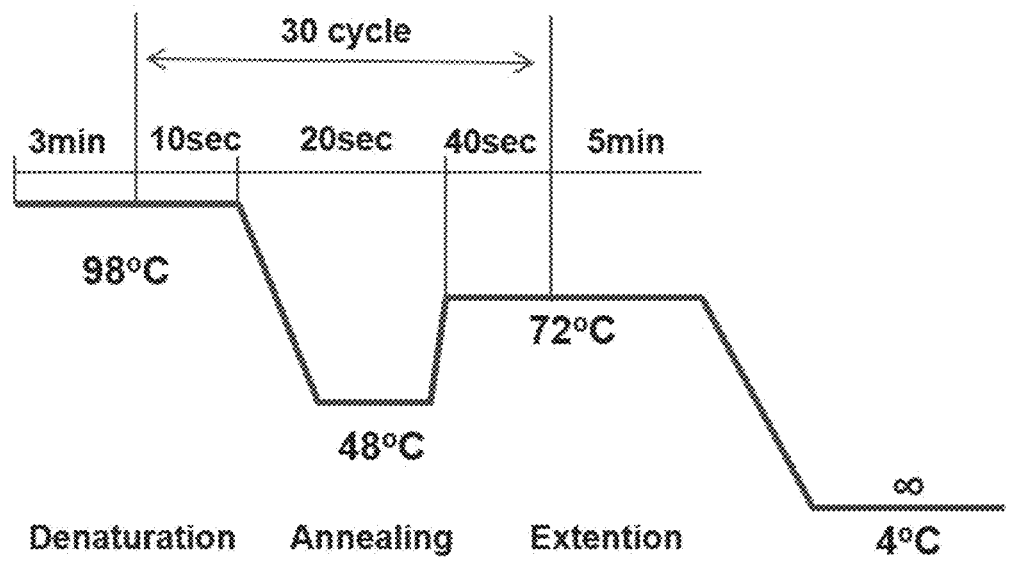

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects.

Hereinafter, the present disclosure will be described in detail.

As a result of having conducted intensive studies on whether DNA extracted by applying microwaves to a biological sample can be used in next generation sequencing, the inventors of the present disclosure confirmed that it is possible to construct a 16s rRNA library and a library for WMS using the extracted DNA and first verified the possibility of constructing a library for next generation sequencing using the sample, and thus completed the present disclosure based on these findings.

Therefore, the present disclosure provides a method for DNA extraction in a biological sample for next generation sequencing (NGS), including the following processes: (1) preparing a mixture by mixing a biological sample with a buffer; (2) applying microwaves to the mixture; and (3) recovering DNA.

In the present disclosure, the biological sample of process (1) may include tissue, cells, whole blood, blood, serum, saliva, soil, water, runny nose, genital mucus, or feces and may be, preferably, feces, but the present disclosure is not limited thereto.

In the present disclosure, the term "buffer" refers to a solution in which a hydrogen ion concentration index (pH) hardly changes even with addition of a strong acid or a strong base, and the buffer may be, preferably, a Tris-EDTA (TE) buffer, but the present disclosure is not limited thereto.

In addition, the mixture of process (1) may have a volume of about 10% to about 42%, preferably, about 20% to about 32%, more preferably, about 25% to about 27%, with respect to the volume of a container (tube).

In addition, the mixture of process (1) may have a concentration of about 100 g/L to about 400 g/L, preferably, about 200 g/L to about 300 g/L, more preferably, about 220 g/L to about 280 g/L.

The term "microwaves" as used herein refers to all electromagnetic radiation having a wavelength of 1 mm to 1 m. Because of its short wavelength, microwaves have almost the same properties as light and have a strong sterilizing power. In general, microwaves often refer to decimeter waves or microwaves having an ultrahigh frequency (UHF) of 300 MHz to 3,000 MHz and centimeter waves having a super-high frequency (SHF) of 2 GHz to 300 GHz. To generate microwaves, special electron tubes, klystrons, magnetrons, lasers, or the like are used, and three-dimensional circuits are mainly used for transmission thereof, and an electronic horn antenna or a parabolic antenna allows emission of microwaves with sharp directivity. Due to having short wavelengths, microwaves are similar to light in terms of properties such as straightness, reflection, refraction, and interference. In the present disclosure, the microwaves may be generated from a product of 2.45 GHz, 700 W, but the present disclosure is not limited thereto.

In addition, the application of microwaves to the mixture may be repeatedly performed more than once, preferably, twice, but the present disclosure is not limited thereto.

In the present disclosure, process (3) may include the following processes: (3-1) centrifuging the resulting mixture obtained in process (2); and (3-2) separating a supernatant from the centrifuged mixture obtained in process (3-1).

According to the present disclosure, it was verified through examples that a library for next generation sequencing, which is capable of representing genetic information of a biological sample, could be constructed within a short time using DNA extracted by applying microwaves to a biological sample.

In one embodiment of the present disclosure, when extracting DNA from a biological sample using microwaves, to maintain a high concentration or purity of the extracted DNA, volume (400 μl corresponding to about 26.6% of a total volume of container) and concentration (250 g/L) conditions of the entire mixture in which a buffer was added to the biological sample, application time (60 seconds) and the number of times (twice) of application of microwaves were identified (see Example 1).

In another embodiment of the present disclosure, as a result of constructing a library for next generation sequencing using DNA extracted from a biological sample using microwaves and analyzing genetic information of the constructed library, in experimental groups consisting of a control (a soil-derived sample, a commercial kit, two PCR cycles), Test 1 (a Canine- or human-derived sample, a commercial kit, and two PCR cycles), and Test 2 (a Canine- or human-derived sample, merged primers, one PCR cycle), in the case of Test 1, the number of raw reads, a QC passed ratio value, and ASV (classification unit) and Shannon (diversity index) values were the highest measured, and the distribution of intestinal microflora was diverse at class and genus levels, and Test 2 exhibited almost the same QC passed ratio value as that of Test 1 (see Example 3).

It was also confirmed that, when using the DNA extraction method using microwaves or merged primers according to the present disclosure, the construction time of a library for next generation sequencing was considerably shortened, compared to the case where an existing commercial kit was used (see Example 3).

The above results confirm that the library for next generation sequencing constructed using the DNA extraction method using microwaves according to the present disclosure is superior in terms of quantity and quality, which suggests that the DNA extraction method using microwaves according to the present disclosure can be usefully applied to next generation sequencing.

Therefore, according to another embodiment of the present disclosure, there is provided a method of constructing a library for next generation sequencing (NGS), including the following processes:

(a) extracting DNA according to the above-described method; (b) amplifying a target DNA using primers; and (c) purifying the amplified product and subjecting the purified product to library pooling.

In addition, the primers of process (b) may be at least one primer pair selected from the group consisting of:

1) a primer consisting of a nucleotide sequence represented by SEQ ID NO: 1; 2) a primer consisting of a nucleotide sequence represented by SEQ ID NO: 2; 3) a primer consisting of a nucleotide sequence represented by SEQ ID NO: 3; 4) a primer consisting of a nucleotide sequence represented by SEQ ID NO: 4; 5) a primer consisting of a nucleotide sequence represented by SEQ ID NO: 5; 6) a primer consisting of a nucleotide sequence represented by SEQ ID NO: 6; 7) a primer consisting of a nucleotide sequence represented by SEQ ID NO: 7; 8) a primer consisting of a nucleotide sequence represented by SEQ ID NO: 8; 9) a primer consisting of a nucleotide sequence represented by SEQ ID NO: 9; 10) a primer consisting of a nucleotide sequence represented by SEQ ID NO: 10; 11) a primer consisting of a nucleotide sequence represented by SEQ ID NO: 11; 12) a primer consisting of a nucleotide sequence represented by SEQ ID NO: 12; 13) a primer consisting of a nucleotide sequence represented by SEQ ID NO: 13; 14) a primer consisting of a nucleotide sequence represented by SEQ ID NO: 14; and 15) a primer consisting of a nucleotide sequence represented by SEQ ID NO: 15.

In this regard, the primers may include a nucleotide sequence with at least 70% homology, for example, at least 80% homology, for example, at least 90% homology, for example, at least 95% homology to the nucleotide sequences represented by SEQ ID NOS: 1 to 15.

Hereinafter, exemplary embodiments will be described to facilitate understanding of the present disclosure. However, the following examples are provided only to facilitate understanding of the present disclosure and are not intended to limit the scope of the present disclosure.

EXAMPLES

Example 1. Identification of DNA Extracted by Applying Microwaves to Biological Sample 1-1. Conditions of DNA Extraction Using Microwaves A DNA extraction method using microwaves does not require the use of specific kits (chemical and physical techniques) and enables DNA extraction only by applying a TE buffer and microwaves and centrifugation, and thus requires less time and money.

However, when DNA is extracted from a biological sample using microwaves, specific conditions were required in the preparation of a biological sample and the application of microwaves to maintain a high concentration or purity of the extracted DNA.

First, to check the maximum volume condition of the mixture, a biological sample (feces) was added to a 1.5 ml tube to which a Tris-EDTA (TE) buffer was added and microwaves were applied thereto after the sample was placed in a rack.

In the case where microwaves are applied to the above-described mixture in which a buffer is added to a biological sample, when a lid of the 1.5 ml tube is opened by pressure, the buffer in the tube is evaporated, and thus effective DNA extraction is impossible.

Thus, to identify conditions for the volume of the entire mixture in which a buffer was applied to a biological sample, each of 200 ul, 300 ul, 400 ul, 500 ul and 600 ul of water was placed in three 1.5 ml tubes, and microwaves were applied to a total of 15 tubes for 1 minute. At this time, a product of 2.45 GHz, 700 W for home use was used as a microwave.

As a result, it was confirmed that the lid of only one of the three tubes with 600 ul of water added thereto and the three tubes with 500 ul of water added thereto was opened, and the lids of the tubes with 200 ul, 300 ul, and 400 ul of water added thereto were not opened. Therefore, an optimal volume of the entire mixture in which a buffer was added to a biological sample was selected on the basis of 400 ul, and conditions that do not exceed a maximum of 500 ul were determined. This is a value in which the volume of the entire mixture corresponds to about 26.6% of the total volume of a container (tube).

In addition, DNA extraction efficiency according to the amount of the biological sample (feces) was examined based on conditions for the volume of the mixture.

More specifically, first, 50 mg, 100 mg, 150 mg, or 200 mg of a biological sample (feces) was added to a 1.5 ml tube and a TE buffer was added thereto so that the volume of the entire mixture reached 400 µl.

Thereafter, the mixture was sufficiently homogenized by vortexing, and after application of microwaves for 60 seconds, left at room temperature for 30 seconds, and then microwaves were applied again thereto for 60 seconds.

Next, after centrifugation in a top table centrifuge at 13,000 rpm for 60 seconds, only a supernatant was transferred to a 1.5 ml tube.

Finally, a TE buffer was added and the resulting mixture was diluted ⅒ to measure the concentration and purity of the extracted DNA using a NANODROP™ One Spectrophotometer manufactured by Thermo Fisher Scientific, and the resulting values were expressed by multiplying by the dilution factor (10). The resulting values are the same as shown in Table 1 below.

TABLE 1

| Fecal amount (mg) | 50 | 50 | 50 | 100 | 100 | 100 |
|---|---|---|---|---|---|---|
| DNA concentration (µg/ml) | 1099.5 | 1096.6 | 808.1 | 1501.9 | 1504.1 | 1089.8 |
| DNA purity (260 nm/230 nm) | 1.20 | 1.20 | 1.21 | 1.18 | 1.18 | 1.20 |

In the case of tubes to which 150 mg of feces and 200 mg of feces were added, measurement was impossible because there was not enough solution left to recover the supernatant or the amount of added TE buffer was not large, and as a result of NANODROP, it was confirmed that the DNA concentration or purity was higher in the case of 100 mg of a biological sample (fecal amount) compared to the fecal amount of 50 mg.

1-2. Confirmation of Whether DNA Extracted Using Microwaves can Represent Intestinal Microflora of Biological Sample To confirm whether the DNA extracted by applying microwaves can represent the type and distribution of intestinal microflora and thus may be used for detection purposes, PCR was performed using primer 341F-R805 targeting 16s rRNA, primer sets targeting the phylum Firmicutes, the phylum Bacteroidetes, the phylum Actinobacteria, the phylum Proteobacteria, the phylum Bifidobacteriaceae, and the phylum Enterobacteriacea and the class *Clostridium* and the class Bacilli and the DNA extracted by applying microwaves of Example 1-1.

More specifically, PCR was performed using DNA extracted from 50 mg of a biological sample (feces) using microwaves under conditions shown in FIG. 1A. A list of primers used in the PCR and information about the primers are shown in Table 2 below.

TABLE 2

| Target | Primer name | Sequence (5'-3') | Length (mer) | Tm (° C.) | % GC | Amplicon size (mer) |
|---|---|---|---|---|---|---|
| 16s RNA (16s) | 341F | CCTACGGGAGCCAGCAG (SEQ ID NO: 16) | 17 | 61.9 | 70 | 444 |
|  | R805 | GACTACHVGGGTATCTAATCC (SEQ ID NO: 17) | 21 | 58.1 | 52 |  |
| Firmicutes (F) | Firm_F | CTGATGGAGCAACGCCGCGT (SEQ ID NO: 18) | 20 | 67.8 | 65 | 429 |
|  | Firm_R | ACACYTAGYACTCATCGTTT (SEQ ID NO: 19) | 20 | 58 | 45 |  |
| Bacteroides (B) | Bact_F | CCGGAWTYATTGGGTTTAAAGGG (SEQ ID NO: 20) | 23 | 55.8 | 43 | 414 |
|  | Bact_R | GGTAAGGTTCCTCGCGTA (SEQ ID NO: 21) | 18 | 57.2 | 55 |  |
| Actinobacteria (A) | Acti_F | GCGKCCTATCAGCTTGTT (SEQ ID NO: 22) | 18 | 55.9 | 50 | 333 |
|  | Acti_R | CCGCCTACGAGCYCTTTACGC (SEQ ID NO: 23) | 21 | 64.4 | 61 |  |
| Proteobacteria (P) | Pro_F | TGGTGTAGGGGTAAAATCCG (SEQ ID NO: 24) | 20 | 57.4 | 50 | 286 |
|  | Pro_R | AGGTAAGGTTCTTCGYGTATC (SEQ ID NO: 25) | 21 | 55.2 | 42 |  |
| Bifidobacteriaceae (B) | Bifi_F | CTCCTGGAAACGGGTGG (SEQ ID NO: 26) | 17 | 58 | 64 | 442 |
|  | Bifi_R | CTTTCACACCRGACGCG (SEQ ID NO: 27) | 17 | 57.1 | 58 |  |
| Enterbacteriaceae (E) | Ente_F | CGTCGCAAGMMCAAAGAG (SEQ ID NO: 28) | 18 | 54 | 50 | 333 |
|  | Ente_R | TTACCGCGGCTGCTGGCAC (SEQ ID NO: 29) | 19 | 67.9 | 68 |  |
| Clostridium (C) | Clos_F | AAAGGAAGATTAATACCGCATA (SEQ ID NO: 30) | 22 | 52.2 | 31 | 538 |
|  | Clos_R | TTCTTCCTAATCTCTACGCA (SEQ ID NO: 31) | 20 | 53.6 | 40 |  |
| Bacilli (B) | Baci_F | GCAGTAGGGAATCTTCCG (SEQ ID NO: 32) | 19 | 59.1 | 57 | 461 |
|  | Baci_R | ACACTTAGCACTCATCGTTT (SEQ ID NO: 33) | 20 | 55.4 | 40 |  |

Next, electrophoresis was performed on a 1.5% agarose gel (100 V, 30 minutes) to confirm PCR amplification products.

Figure 1B:
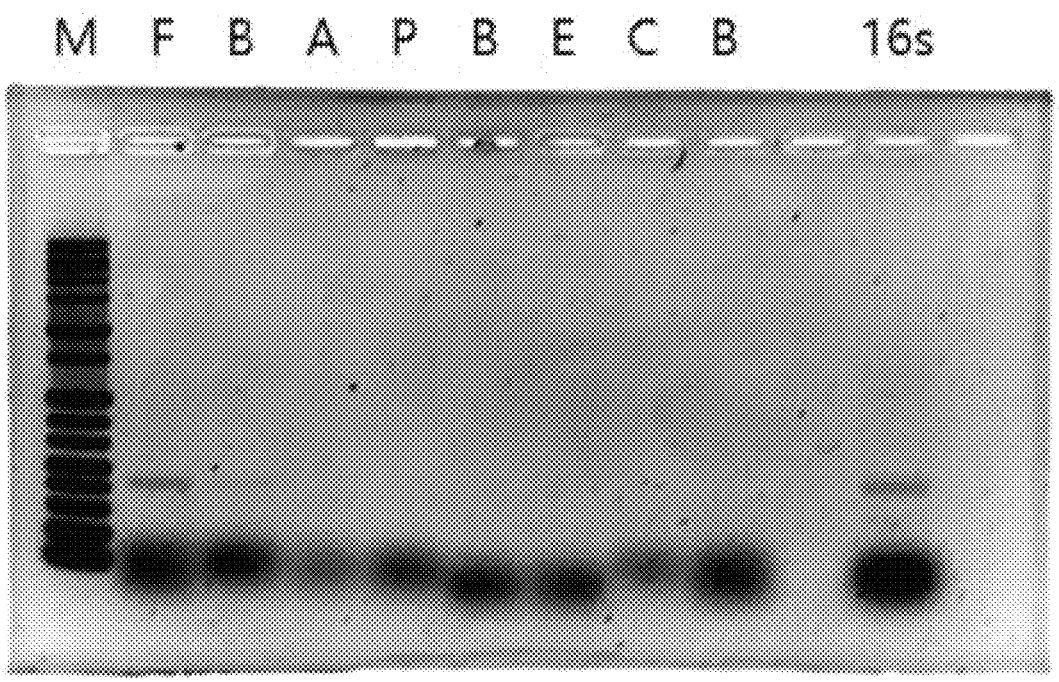

As a result, as shown in FIG. 1B, it was confirmed that specific bands between 400 base pairs (bp) and 500 bp were shown from DNA extracted by applying microwaves in the phylum Firmicutes and the phylum Bacteroidetes, which are the main phylum of intestinal microflora and the housekeeping gene 16s rRNA.

The above results indicate that, when PCR is performed using the DNA extracted by applying microwaves, the DNA represents intestinal microflora of the biological sample (feces) to a certain extent, and it was confirmed that the DNA extracted by applying microwaves could also be applied to NGS.

Example 2. Confirmation of Possibility of Constructing Library Using DNA Extracted Using Microwaves To construct a 16s rRNA library using DNA extracted using microwaves, 0 Illumina NEXTERA XT Index, which is a commercial kit, or merged primers, which are novel merged primers according to the present disclosure, were used.

2-1. Confirmation of Possibility of Constructing 16s rRNA Library Using Illumina NEXTERA XT Index Two PCR cycles and two DNA purification processes were performed in accordance with Illumina NEXTERA XT guidelines, and analysis was performed using TAPESTATION D1000 Screen Tape.

Figure 2A:
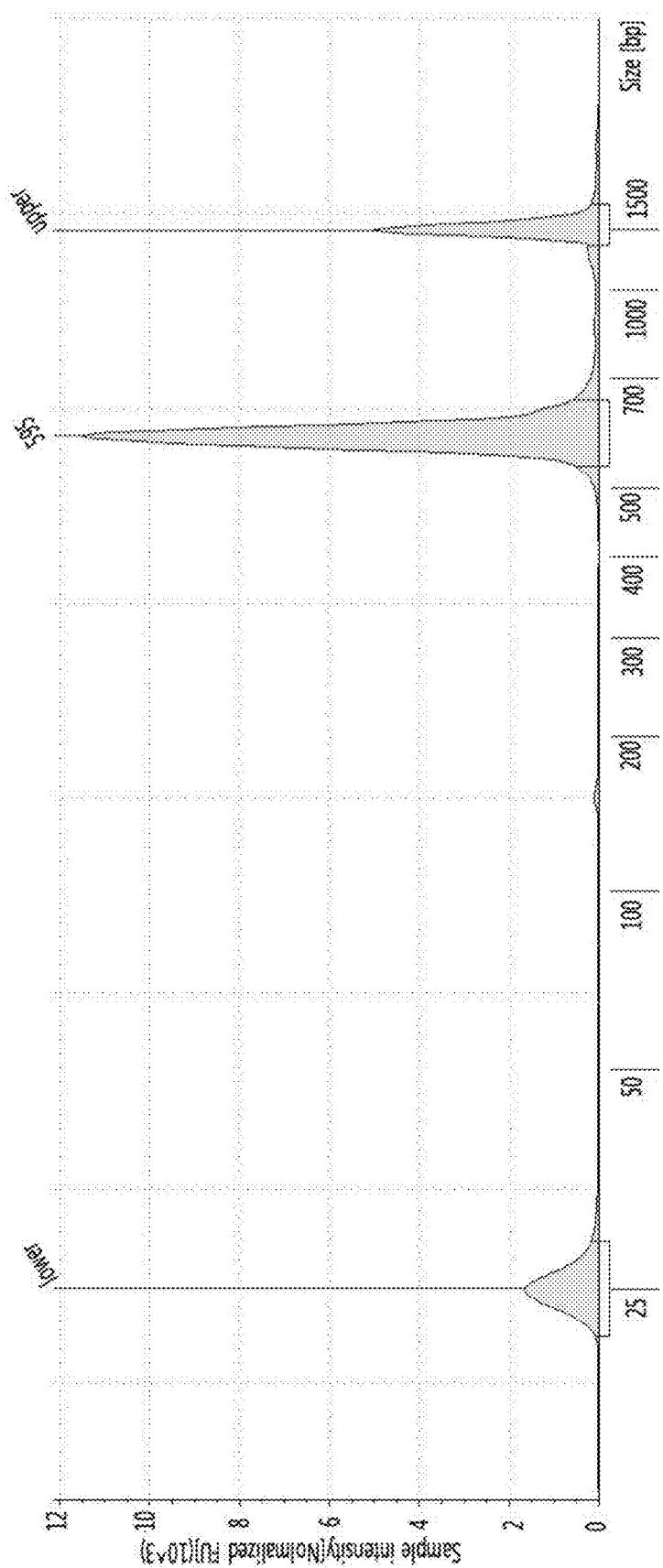
Figure 2B:
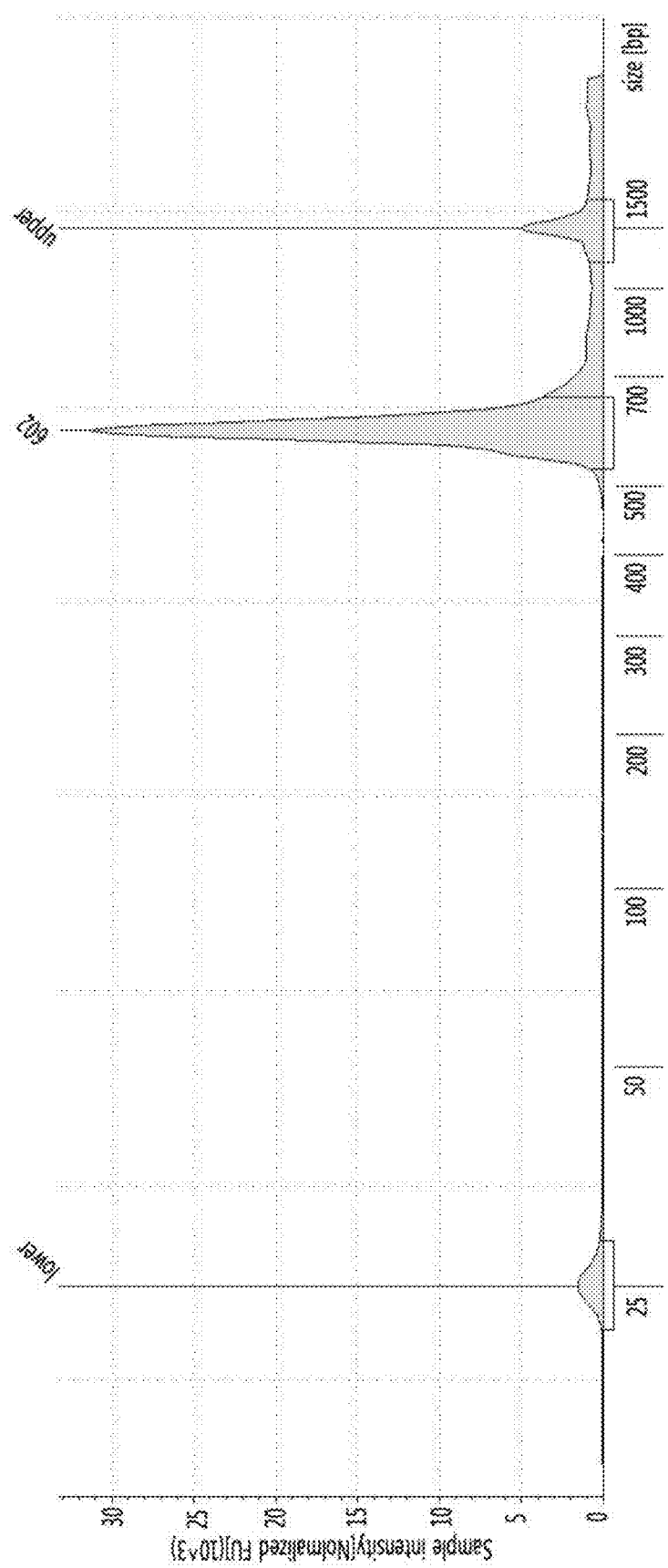
Figure 2C:
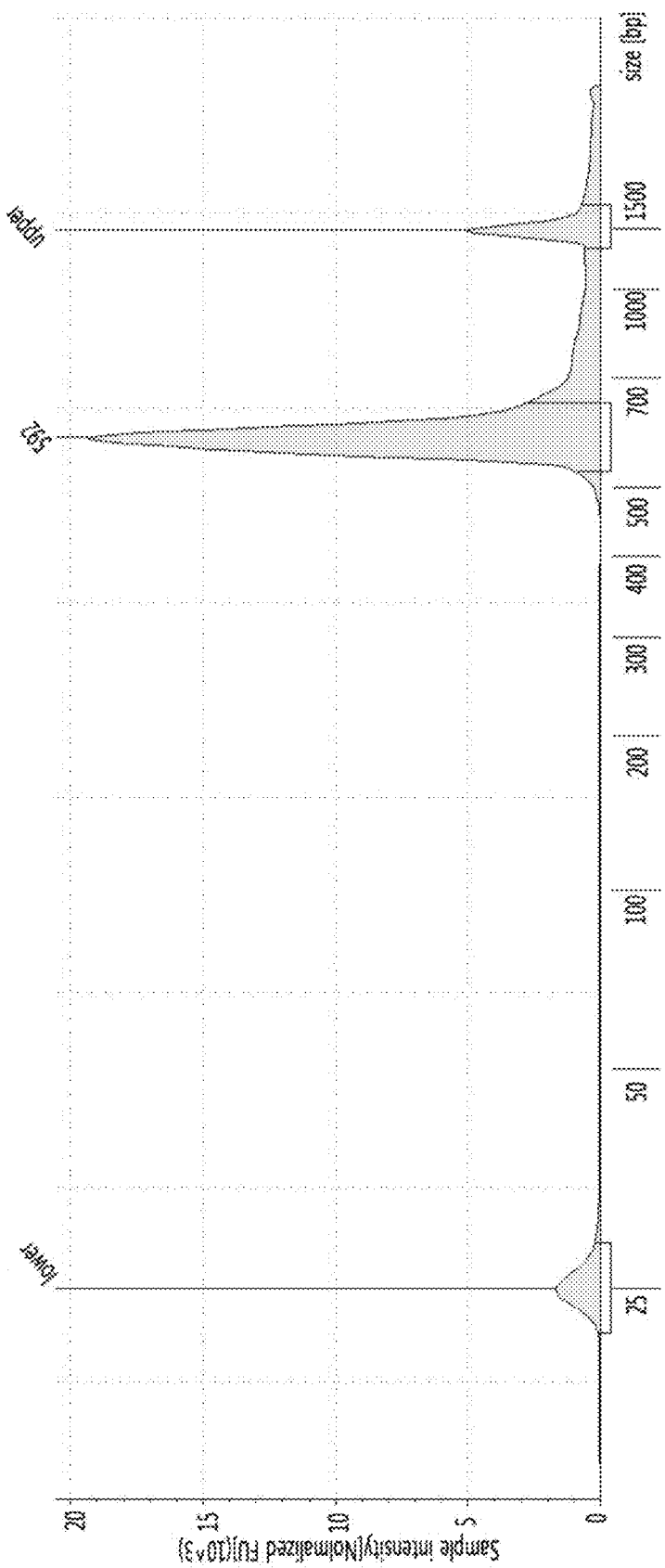

As a result, as shown in FIGS. 2A to 2C, it was confirmed that an appropriate size of the library and the concentration thereof were measured as being 595 bp and 27.99 ng/ul, respectively in FIG. 2A, an appropriate size of the library and a concentration thereof were measured as being 602 bp and 94.59 ng/ul, respectively in FIG. 2B, and an appropriate size of the library and a concentration thereof were measured as being 592 bp and 68.74 ng/ul, respectively in FIG. 2C.

The above results indicate that it is sufficiently possible to construct a 16s rRNA library using DNA extracted by applying microwaves and a commercial kit (Illumina NEXTERA XT).

2-2. Confirmation of Possibility of Constructing 16s rRNA Library Using Novel Merged Primer According to Present Disclosure In the present disclosure, to construct a library through only a single PCR process, merged primers containing sequences (index, linker, target region, overhang, and the like) required for performing NGS as described below was constructed. A list of merged primers is shown in Table 3 below.

TABLE 3

| Primer name | Sequences (5'-3') | SEQ ID NO: |
|---|---|---|
| MS_502 | AATGATACGGCGACCACCGAGATCTACACCTCTCTATTCGTCGGCAGCGT CAGATGTGTATAAGAGACAGCCTACGGGAGGCAGCAG | 1 |
| MS_503 | AATGATACGGCGACCACCGAGATCTACACTATCCTCTTCGTCGGCAGCGT CAGATGTGTATAAGAGACAGCCTACGGGAGGCAGCAG | 2 |
| MS_505 | AATGATACGGCGACCACCGAGATCTACACGTAAGGAGTCGTCGGCAGCGT CAGATGTGTATAAGAGACAGCCTACGGGAGGCAGCAG | 3 |
| MS_513 | AATGATACGGCGACCACCGAGATCTACACTCGACTAGTCGTCGGCAGCGT CAGATGTGTATAAGAGACAGCCTACGGGAGGCAGCAG | 4 |
| MS_515 | AATGATACGGCGACCACCGAGATCTACACTTCTAGCTTCGTCGGCAGCGT CAGATGTGTATAAGAGACAGCCTACGGGAGGCAGCAG | 5 |
| MN_701 | CAAGCAGAAGACGGCATACGAGATTCGCCTTAGTCTCGTGGGCTCGGAGA TGTGTATAAGAGACAGGACTACHVGGGTATCTAATCC | 6 |
| MN_701 | CAAGCAGAAGACGGCATACGAGATCTAGTACGGTCTCGTGGGCTCGGAGA TGTGTATAAGAGACAGGACTACHVGGGTATCTAATCC | 7 |
| MN_703 | CAAGCAGAAGACGGCATACGAGATTTCTGCCTGTCTCGTGGGCTCGGAGA TGTGTATAAGAGACAGGACTACHVGGGTATCTAATCC | 8 |
| MN_704 | CAAGCAGAAGACGGCATACGAGATGCTCAGGAGTCTCGTGGGCTCGGAGA TGTGTATAAGAGACAGGACTACHVGGGTATCTAATCC | 9 |
| MN_705 | CAAGCAGAAGACGGCATACGAGATAGGAGTCCGTCTCGTGGGCTCGGAGA TGTGTATAAGAGACAGGACTACHVGGGTATCTAATCC | 10 |
| MN_706 | CAAGCAGAAGACGGCATACGAGATCATGCCTAGTCTCGTGGGCTCGGAGA TGTGTATAAGAGACAGGACTACHVGGGTATCTAATCC | 11 |
| MN_707 | CAAGCAGAAGACGGCATACGAGATGTAGAGAGGTCTCGTGGGCTCGGAGA TGTGTATAAGAGACAGGACTACHVGGGTATCTAATCC | 12 |
| MN_708 | CAAGCAGAAGACGGCATACGAGATCCTCTCTGGTCTCGTGGGCTCGGAGA TGTGTATAAGAGACAGGACTACHVGGGTATCTAATCC | 13 |
| MN_709 | CAAGCAGAAGACGGCATACGAGATAGCGTAGCGTCTCGTGGGCTCGGAGA TGTGTATAAGAGACAGGACTACHVGGGTATCTAATCC | 14 |
| MN_710 | CAAGCAGAAGACGGCATACGAGATCAGCCTCGGTCTCGTGGGCTCGGAGA TGTGTATAAGAGACAGGACTACHVGGGTATCTAATCC | 15 |

Figure 3A:
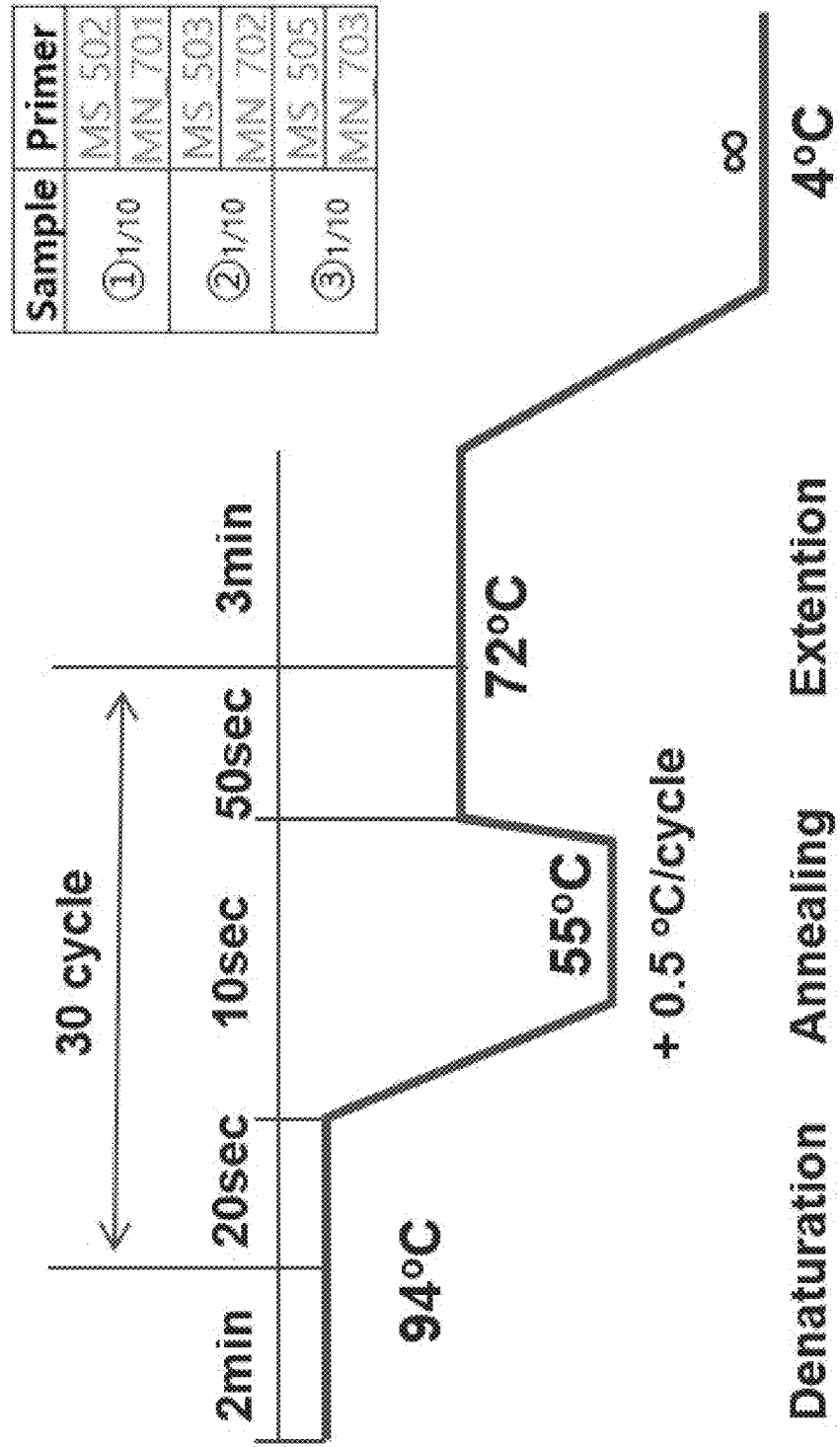

Existing HERCULASE II Fusion DNA Polymerase manufactured by Agilent was used as a PCR kit, and PCR was performed using, as a DNA template, each of the samples ($①_{1/10}$, $②_{1/10}$, and $③_{1/10}$) obtained by diluting the DNA extract treated with microwaves to a level of ⅒, as illustrated in FIG. 3A. In this regard, $①_{1/10}$ used primers of SEQ ID NOS: 1 and 6, $②_{1/10}$ used primers of SEQ ID NOS: 2 and 7, and $③_{1/10}$ used primers of SEQ ID NOS: 3 and 8.

More specifically, a specific annealing temperature was fixed at the time of PCR and as illustrated in FIG. 3A, a gradient PCR technique was used. In addition, library QC was analyzed using TAPESTATION D1000 Screen Tape.

Figure 3B:
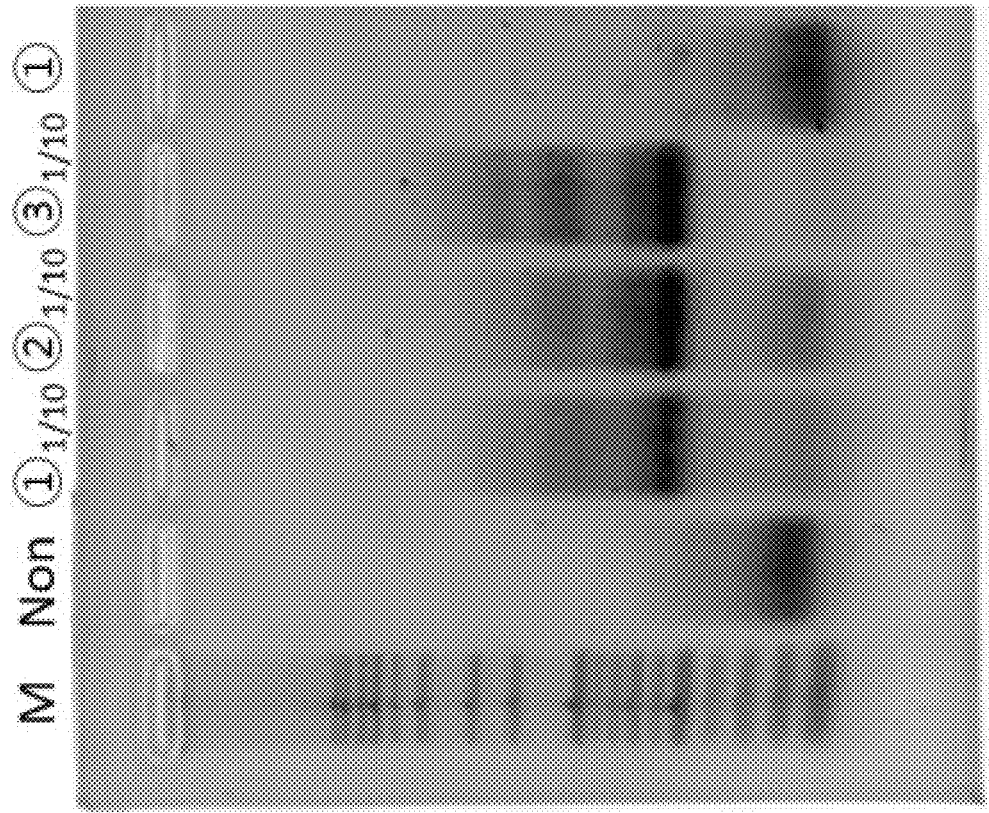

As a result, as shown in FIG. 3B, it was confirmed that an amplicon with a size of 500 bp to 600 bp was well amplified, and it was also confirmed that, when PCR was performed using an undiluted DNA extract (no dilution) ① treated with microwaves, only a band with a size of 100 bp to 200 bp, which is assumed to be a primer dimer as in "Non" in which a DNA template was not added was amplified.

Figure 4A:
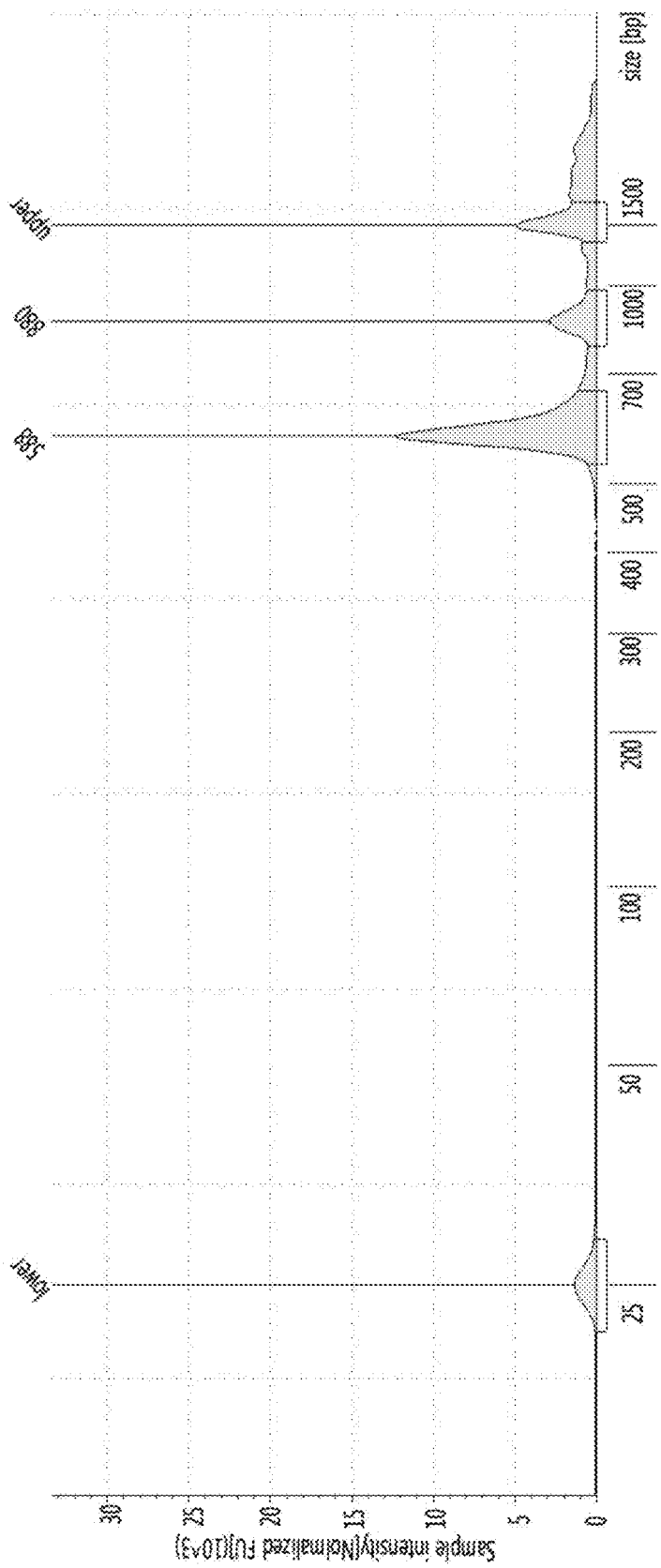
Figure 4B:
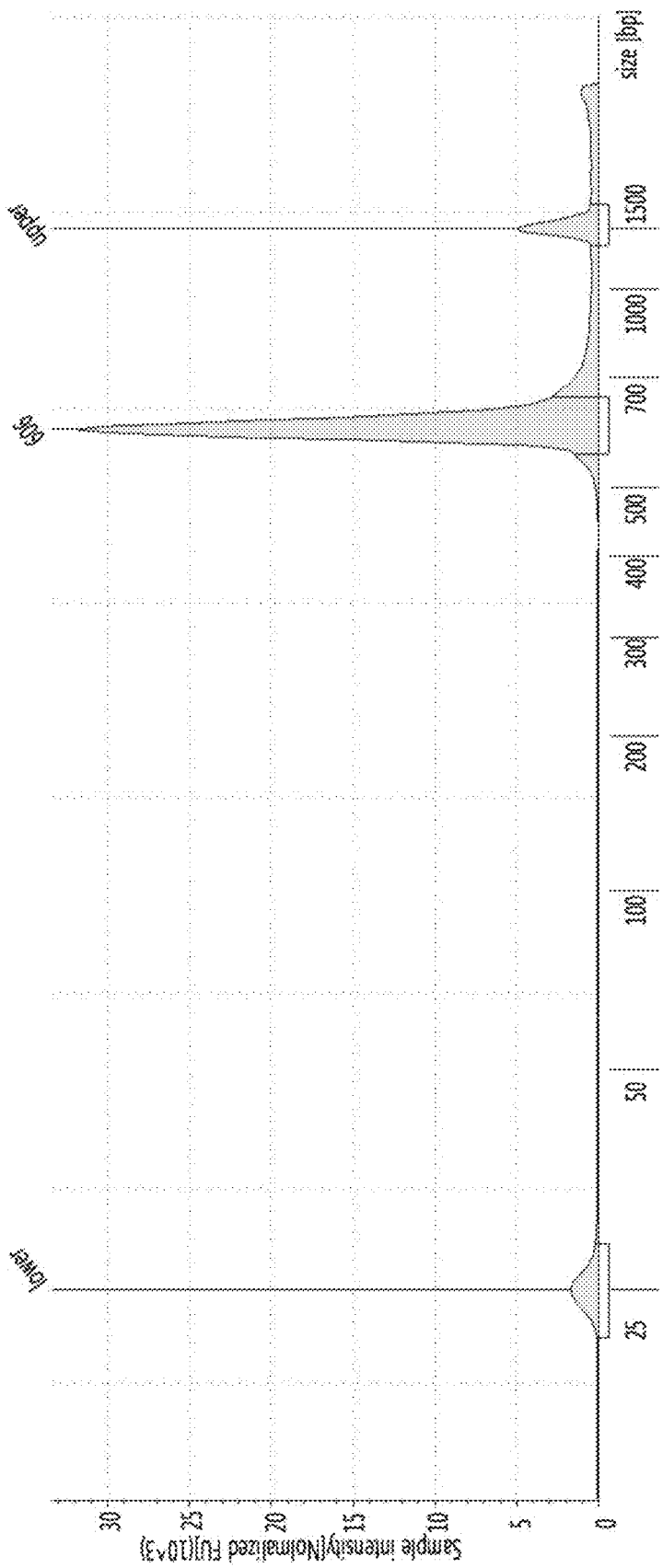
Figure 4C:
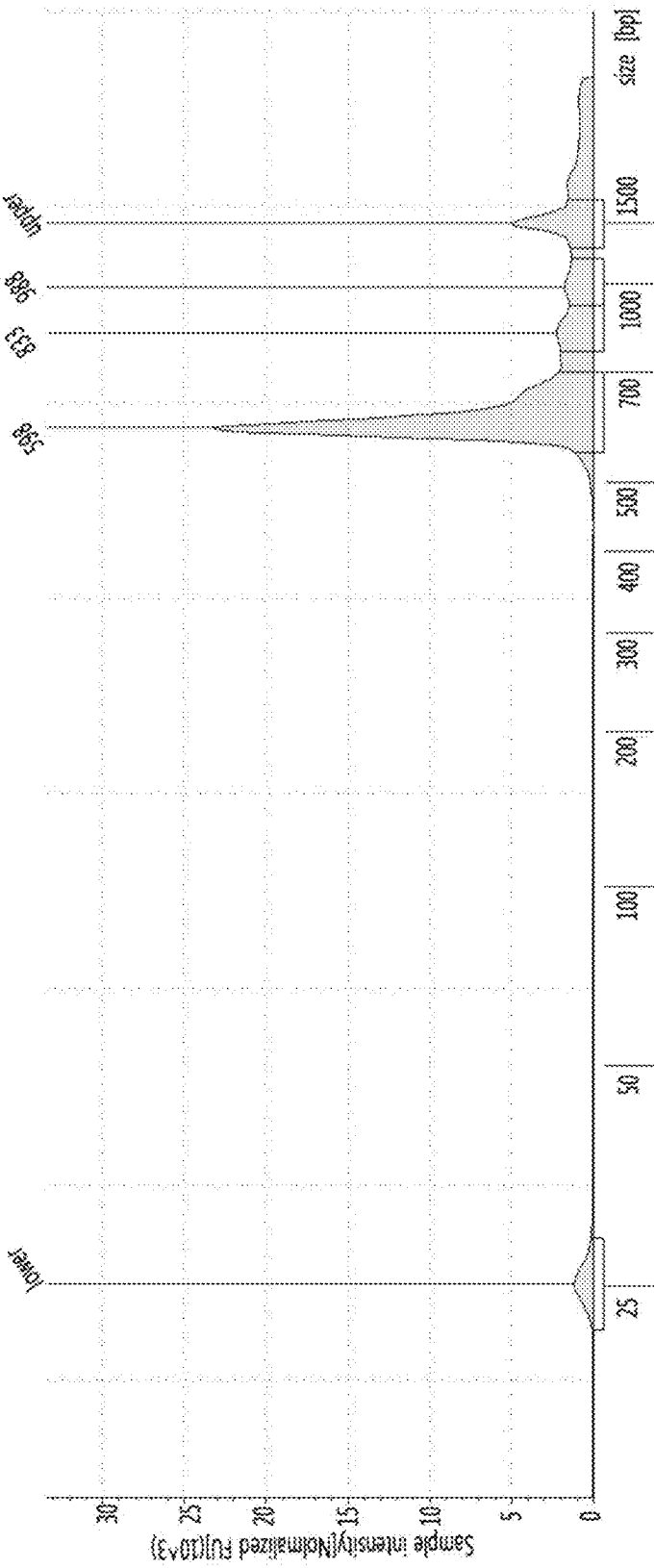

In addition, as illustrated in FIGS. 4A to 4C, it was confirmed that the DNA size and concentration of the library were measured as being 588 bp and 20.92 ng/ul, respectively in FIG. 4A ($①_{1/10}$), the DNA size and concentration of the library were measured as being 606 bp and 55.61 ng/ul, respectively in FIG. 4B ($②_{1/10}$), and the DNA size and concentration of the library were measured as being 598 bp and 33.03 ng/ul, respectively in FIG. 4C ($③_{1/10}$).

The above results indicate that, as with a commercial kit (index), it is possible to construct a 16s rRNA library only through a single PCR process using the DNA extracted by applying microwaves and merged primers according to the present disclosure.

2-3. Confirmation of Possibility of Constructing Library for Whole Metagenomic Sequencing (WMS) Using DNA Extracted Using Microwaves It was examined whether gDNA extracted by applying microwaves can also be used to construct a library for WMS as well as the 16s rRNA library.

Meanwhile, whole metagenomic sequencing (WMS) is a technique for identifying "all untargeted microbial genomes" in a specific sample, in which the sample is pretreated through the following processes: tagmentation whereby DNA in the sample is digested to an appropriate size; elongation using primers having index sequences; and amplification. Unlike the pretreatment method for a biological sample to construct a 16s rRNA library, the DNA tagmentation process by transposomes must be performed under appropriate DNA input and appropriate temperature and time conditions, and DNA purity is also very important.

Thus, microwaves were applied to a biological sample for constructing a library for WMS, followed by DNA purification, and the DNA sample was used to construct a library for WMS.

Meanwhile, commercialization kits mainly used for WMS are ① NEXTERA XT and ② NEXTERA DNA Flex, which are manufactured by Illumina, and the biggest difference therebetween is that the optimized DNA supply amount is 1 ng for XT, whereas it is 1 ng to 500 ng for Flex, indicating whether it is affected in the accuracy of DNA quantification. The reason for using the commercial kit is because a method for DNA extraction by applying microwaves is somewhat inferior to commercial kits in terms of DNA yield or purity. In the present disclosure, a single commercial kit was used to propose the possibility of constructing a WMS library for an extract obtained using microwaves, but whether or not a commercial kit is used or the type thereof are not limited.

An experiment was performed using each of 1 ng and 10 ng (measurement values using QUBIT) of samples obtained by extracting DNA by applying microwaves and then purifying the extracted DNA using WIZARD® SV Gel and PCR Clean-Up System available from Promega in accordance with the guidelines of the corresponding kit, and then library QC was analyzed using TAPESTATION D1000 Screen Tape.

Figure 5A:
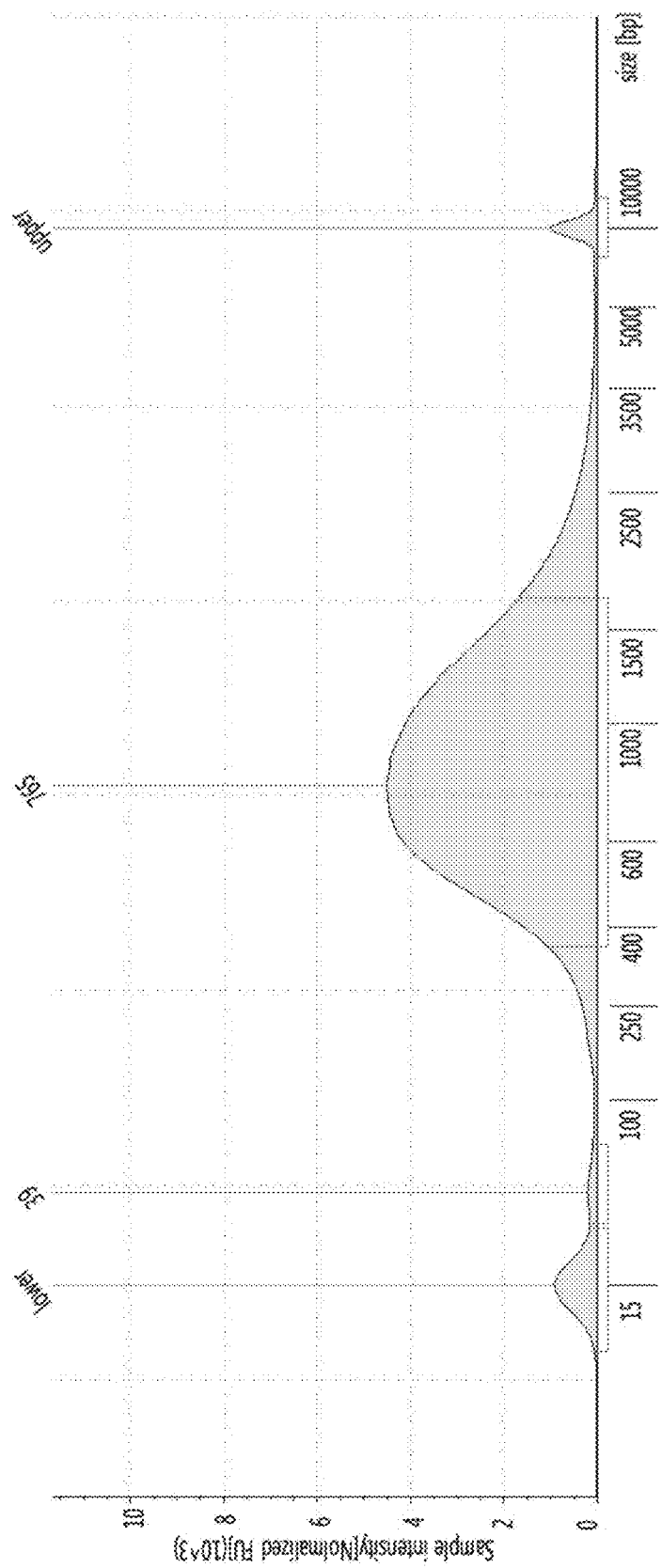

As a result, as illustrated in FIGS. 5A and 5B, it was confirmed that the DNA size, DNA concentration, and molar concentration of a library constructed using an Illumina NEXTERA XT kit were measured as being 810 bp, 8.44 ng/ul, and 16.03 nM, respectively in FIG. 5A, and the DNA size, DNA concentration, and molar concentration of a library constructed using an Illumina NEXTERA DNA Flex kit were measured as being 584 bp, 8.04 ng/ul, and 21.19 nM, respectively in FIG. 5B.

From the above results, it is confirmed that it is possible to construct a library for WMS using DNA extracted by applying microwaves.

Example 3. Confirmation of Genetic Information Analysis Results of Library for Next Generation Sequencing Constructed Using DNA Extracted Using Microwaves Based on Example 2, a library for next generation sequencing was constructed using a method of DNA extraction in a sample for next generation sequencing (NGS) according to the present disclosure and the obtained resultant was analyzed.

Figure 6:
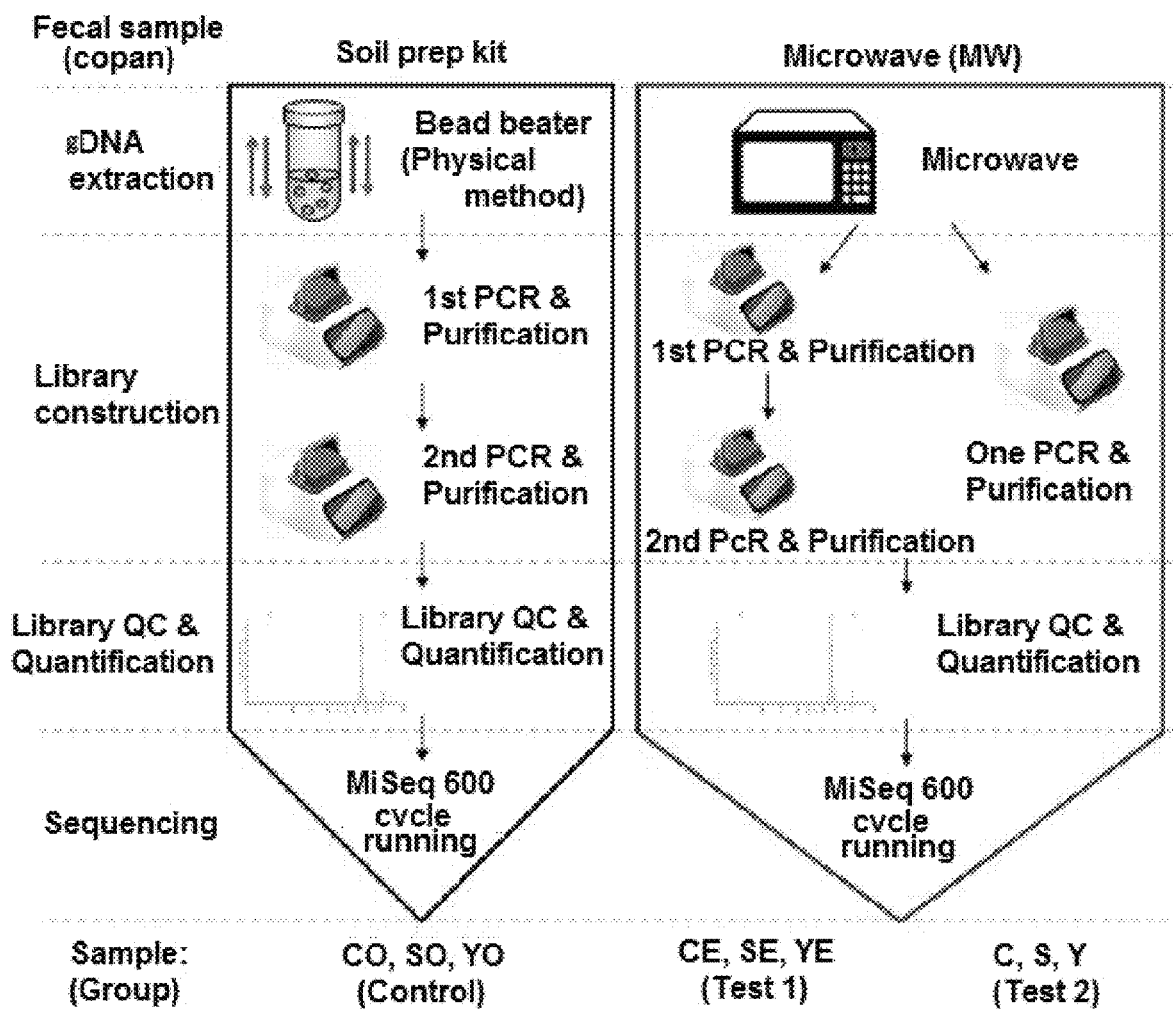
FIG. 6 is a schematic diagram illustrating an experimental design for confirming the applicability of DNA extracted by applying microwaves to next generation sequencing.

More specifically, as shown in Table 4 below, experimental groups were divided into three groups, and biological samples for each experimental group were Canine (female, 8 months old), human (female, 20 months old), and human (female, 30 months old). That is, a total of 9 experimental groups were used for the entire experiment. An experimental method is the same as shown in FIG. 6.

TABLE 4

|  |  | Sample | | |
| --- | --- | --- | --- | --- |
| Group | Method | Canine (F, 8 M) | Human (F, 20 M) | Human (F, 30 M) |
| Control, soil (O) | Soil prep + two step PCR | CO | SO | YO |
| Test 1 (E) | Microwave + two step PCR | CE | SE | YE |
| Test 2 | Microwave + one step PCR | C | S | Y |

The experimental results were results obtained by constructing a library for next generation sequencing using Illumina MISEQ and analyzing 16s rRNA of fecal (intestinal) microflora. More specifically, analysis was performed using a DADA2 program based on an amplicon sequence variant (ASV) enabling high-resolution analysis.

Figure 7A:
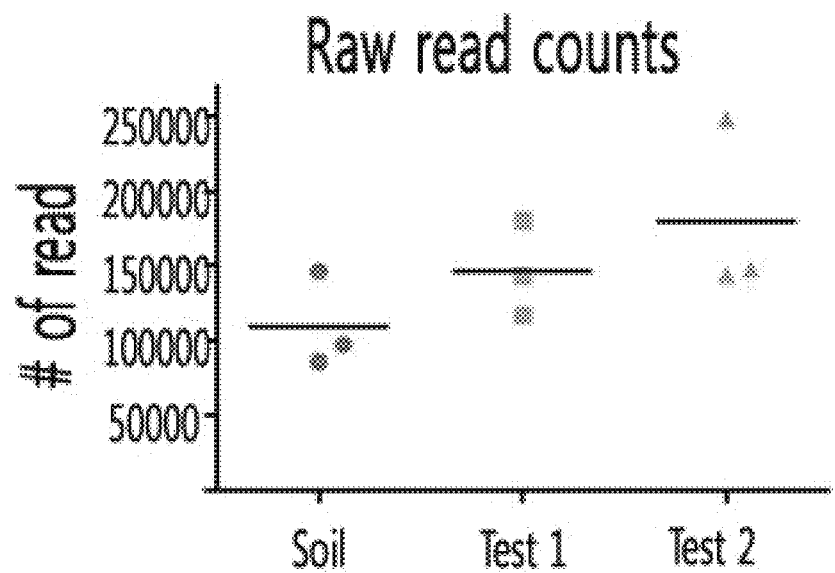

3-1. Confirmation of Number of Raw Reads and Analysis Results of QC Passed Ratio As illustrated in FIG. 7A, it was confirmed that the number of raw reads was measured as being 109,752 for control (soil), 146,197 for test 1, and 179,659 for test 2, on average. The number of produced raw reads was greater in the order of test 2, test 1, and control.

Figure 7B:
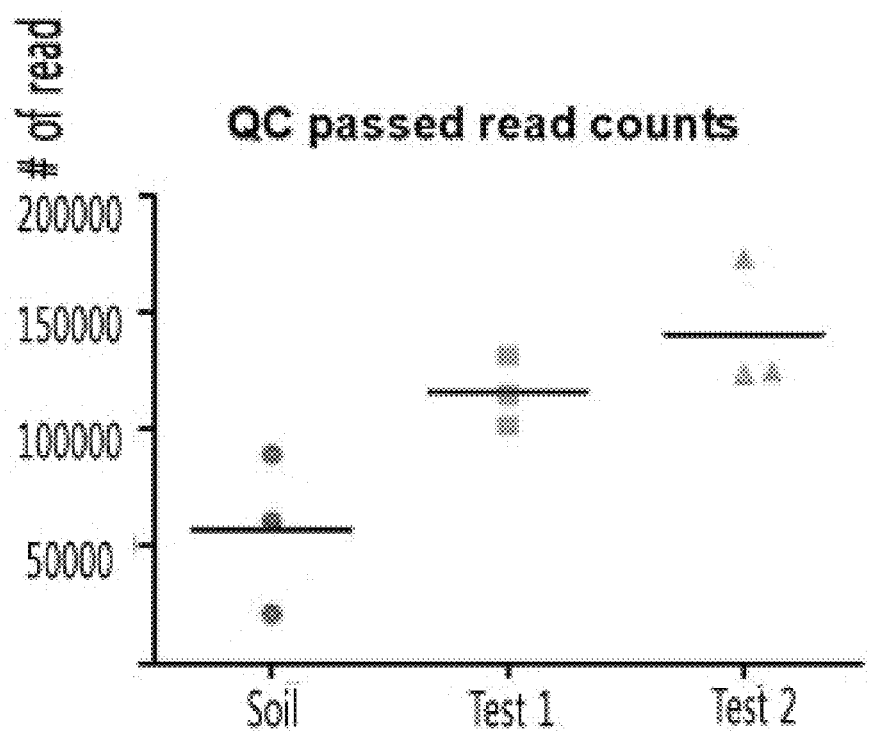
Figure 7C:
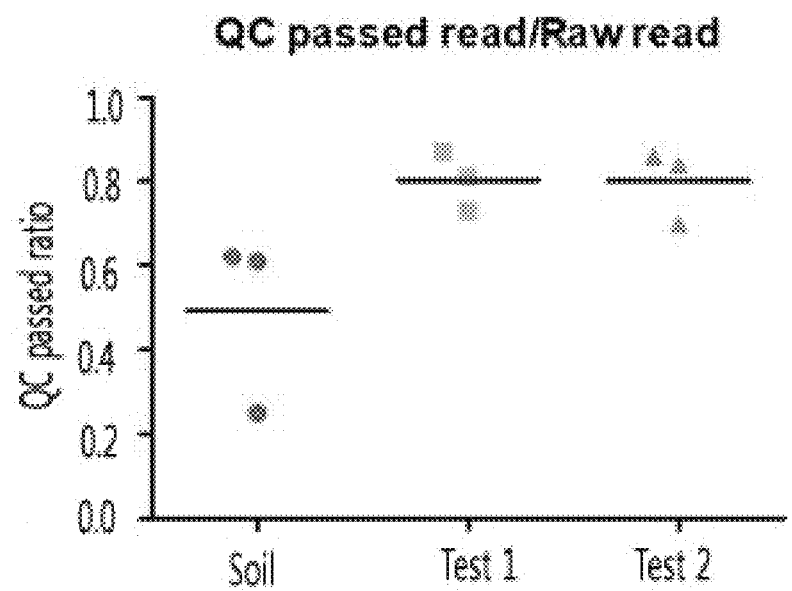

In contrast, as illustrated in FIG. 7C, QC passed ratios were measured as being 49.3% for control (soil), 80.3% for test 1, and 80% for test 2, from which it was confirmed that the QC passed ratios of test 1 and test 2 were almost similar, control (soil) exhibited a level of 50% or less.

As illustrated in FIG. 7B, it was also confirmed that the average number of QC passed reads was measured as being 57,068 for control (soil), 116,024 for test 1, and 170,639 for test 2.

3-2. Confirmation of Analysis Results of ASV and Shannon Values

As values for data obtained by quantification of the constructed library through qRT-PCR and running of the same DNA equivalents in the same lane, ASVs representing classification units and Shannon values representing diversity indexes were analyzed.

Figure 8A:
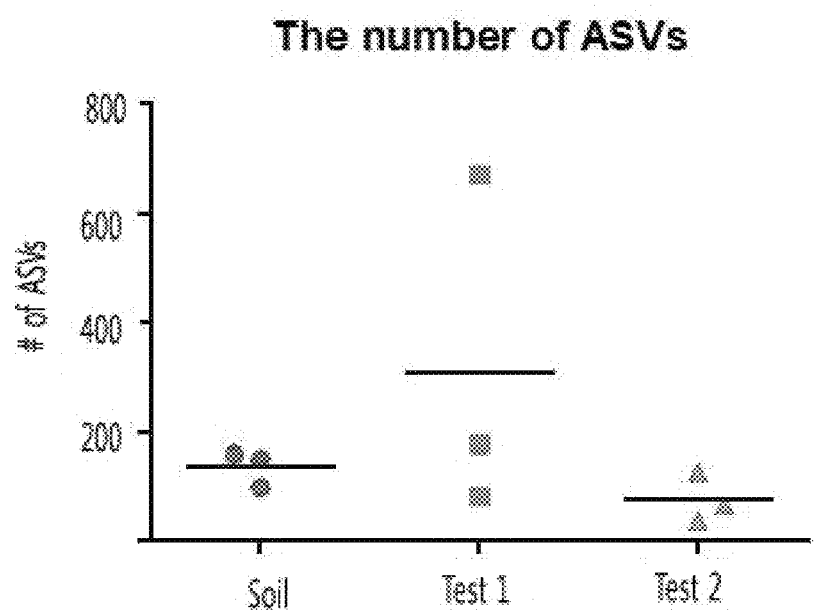
Figure 8B:
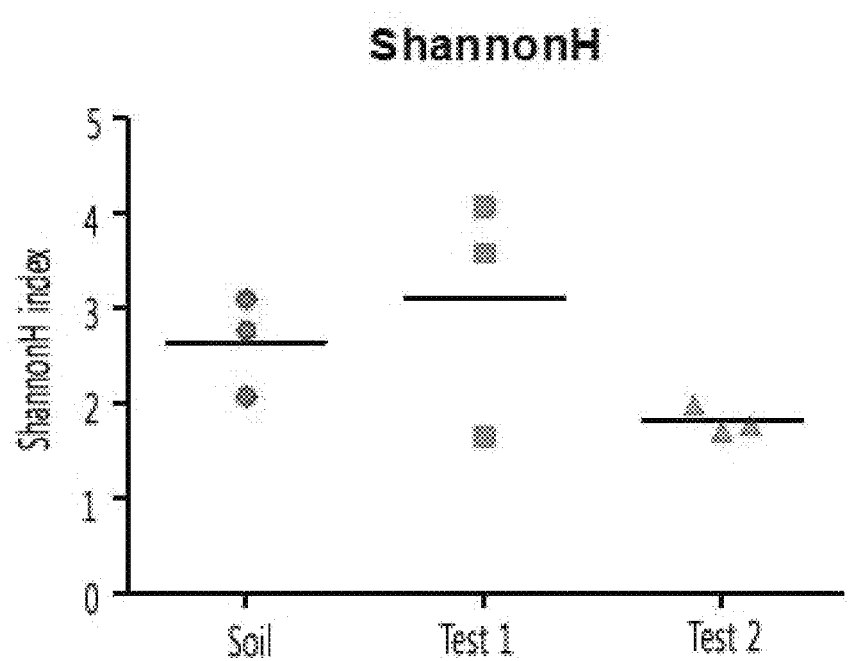
Figure 8C:
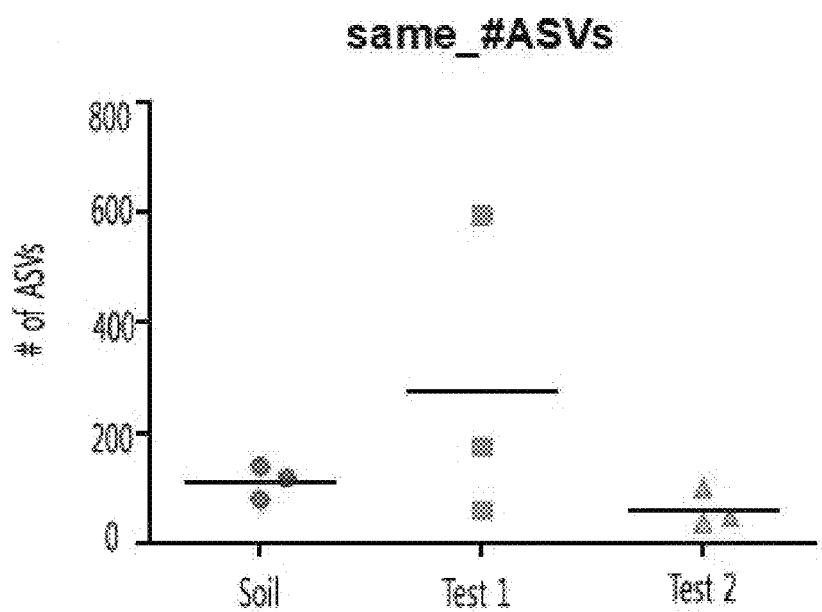
Figure 8D:
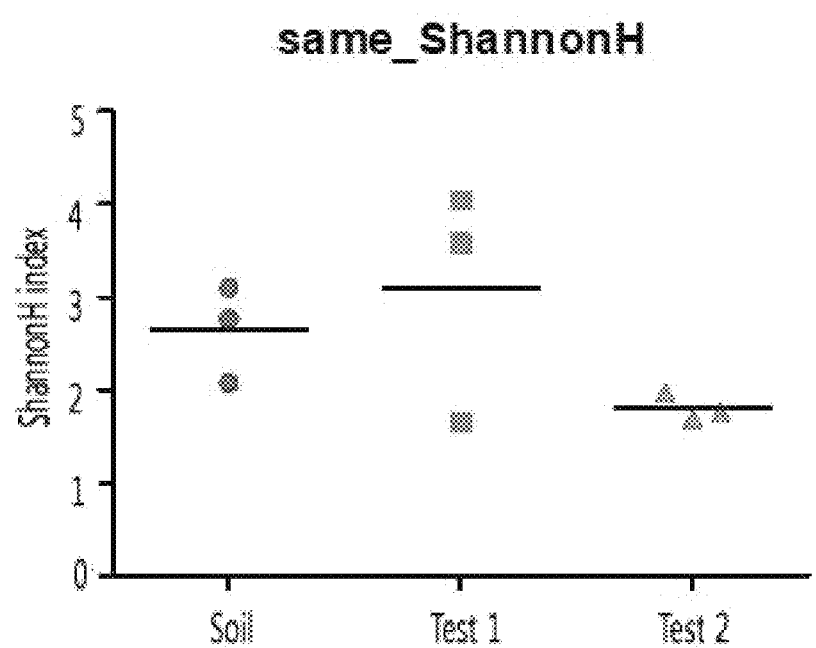

As a result, as illustrated in FIGS. 8A and 8C, it was confirmed that although there was not much difference in the number of ASVs using QC passed total reads for each biological sample and each experimental group or randomly selected 10,000 reads, the values of test 2 were lower than those of control (soil) and the values of test 1 were greater than those of control (soil) and test 2.

It was also confirmed that, although there was no much difference in Shannon index between the biological samples and between the experimental groups regardless of reads used in FIGS. 8B and 8C, the values of test 2 were lower than control (soil) and the values of test 1 were greater than control (soil) and test 2.

From the above results, it was confirmed that the sequencing throughput using DNA extracted by applying microwaves was higher than that of control (soil).

3-3. Confirmation of Distribution Analysis of Library Based on DNA Extracted from Each Biological Sample at Class and Genus Levels For a sample control (CO) of Canine (female, 8 months old), test 1 (CE), and test 2 (C), the distribution of intestinal microflora was analyzed at class and genus levels.

Figure 9A:
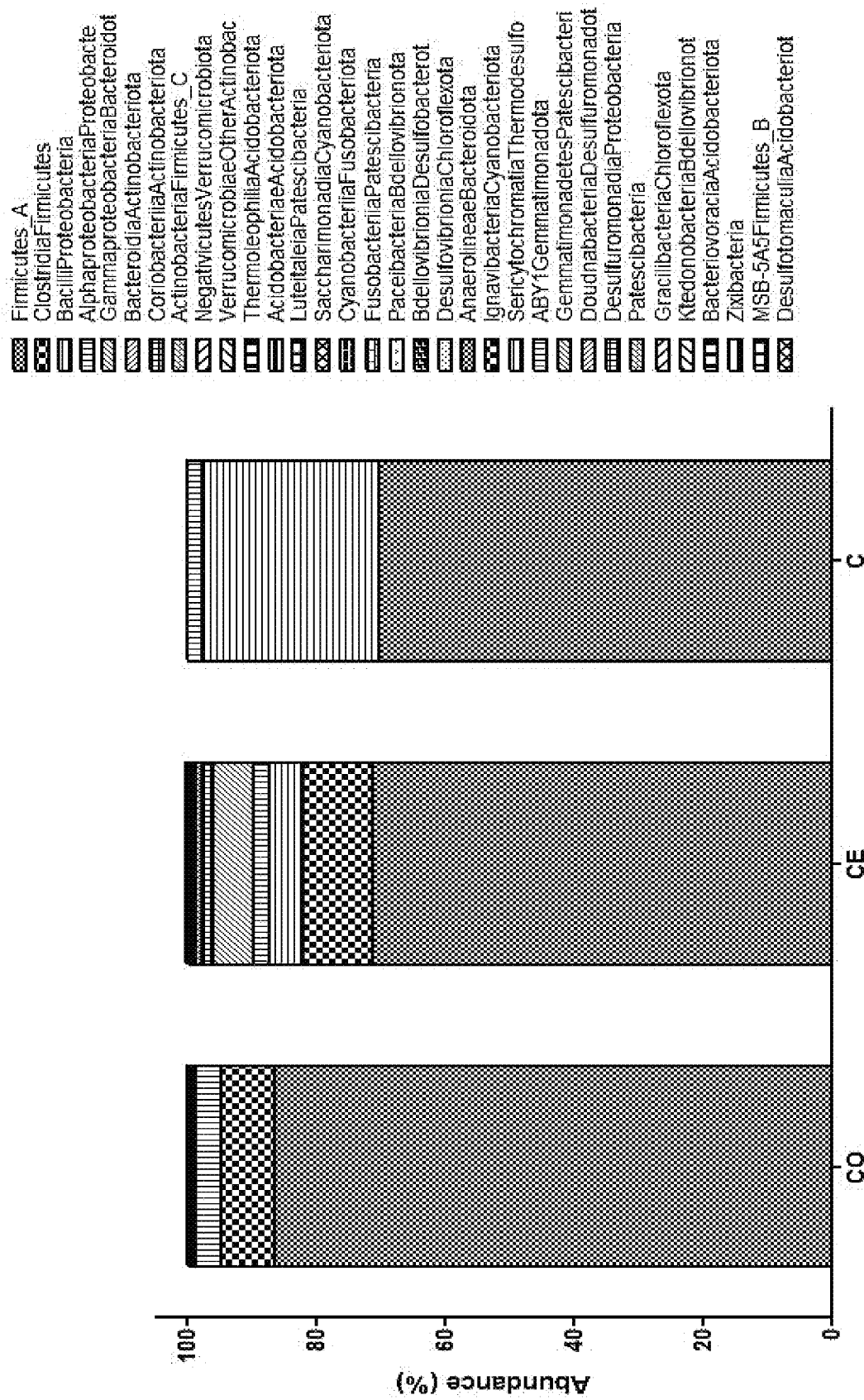
Figure 9B:
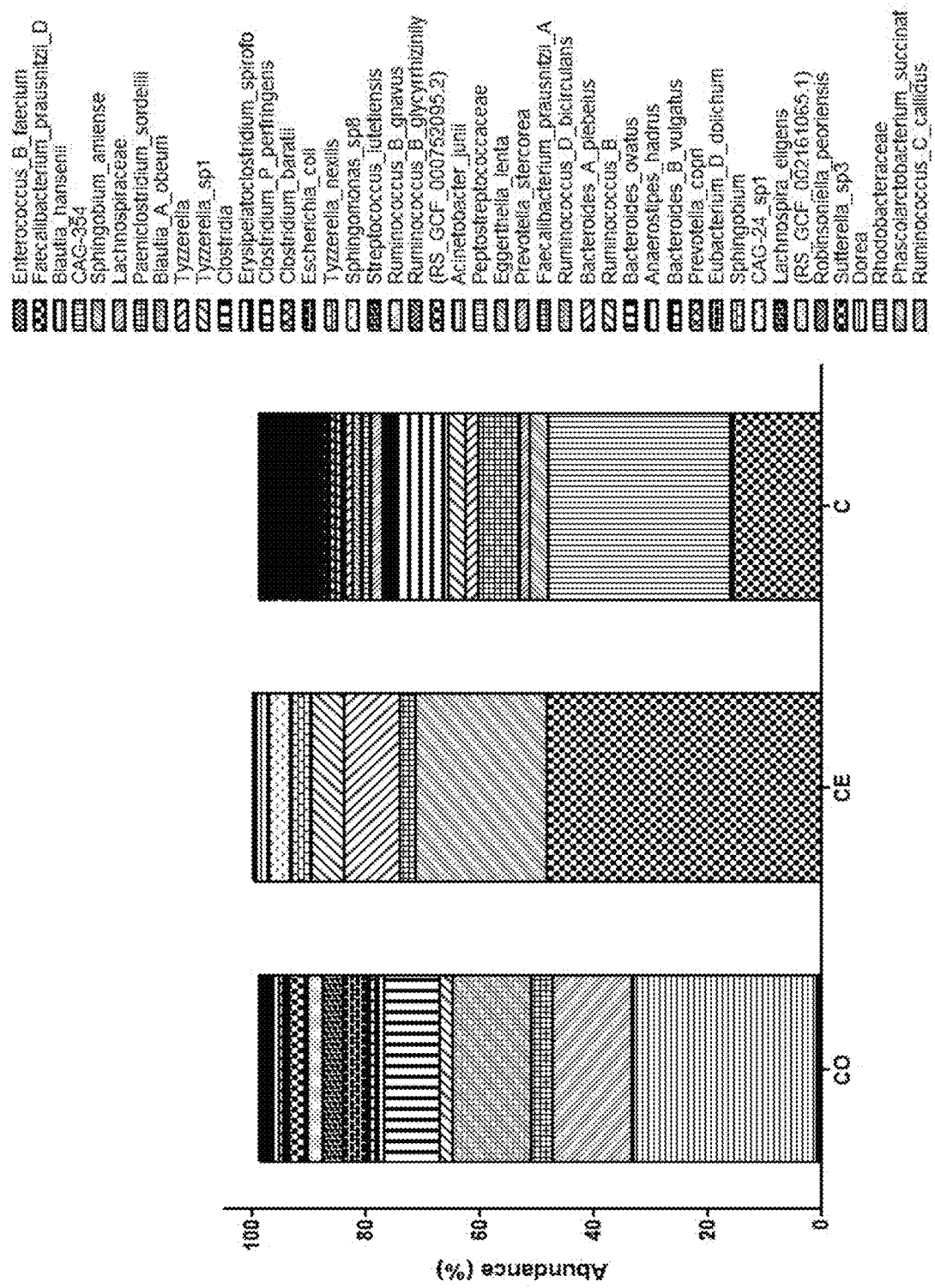

As a result, as illustrated in FIGS. 9A and 9B, the distribution of microflora for the sample control (CO) of Canine (female, 8 months old), test 1 (CE), and test 2 (C) was confirmed at class and genus levels. More specifically, as shown in FIG. 9A, the distribution of control (CO) was similar to the distribution of test 1 (CE) at the class level, and it was confirmed that, as main classes, the class Clostridia (86.4%, 70.1%, 71.3%) and Bacilli (8.2%, 0%, 10.7%) of Firmicutes, and the class Alphaproteobacteria (0%, 27.7%, 5.2%) of Proteobacteria were present.

In addition, as illustrated in FIG. 9B, it was confirmed that the differences between the experimental groups were shown to be very large at the genus level, and, as main genera, the genus *Blautia hansenii* (32.3%, 0.4%, 0%), the genus *Faecalibacterium prausnitzii* (0.3%, 15.4%, 48.1%), the genus *Clostridia* CAG-354 (0.2%, 32.1%, 0%), and the genus *Sphingobium amiense* (0%, 3.2%, 23.2%) were present.

For a sample control (CO) of human (female, 20 months old), test 1 (CE), and test 2 (C), the distribution of intestinal microflora was analyzed at class and genus levels.

Figure 10A:
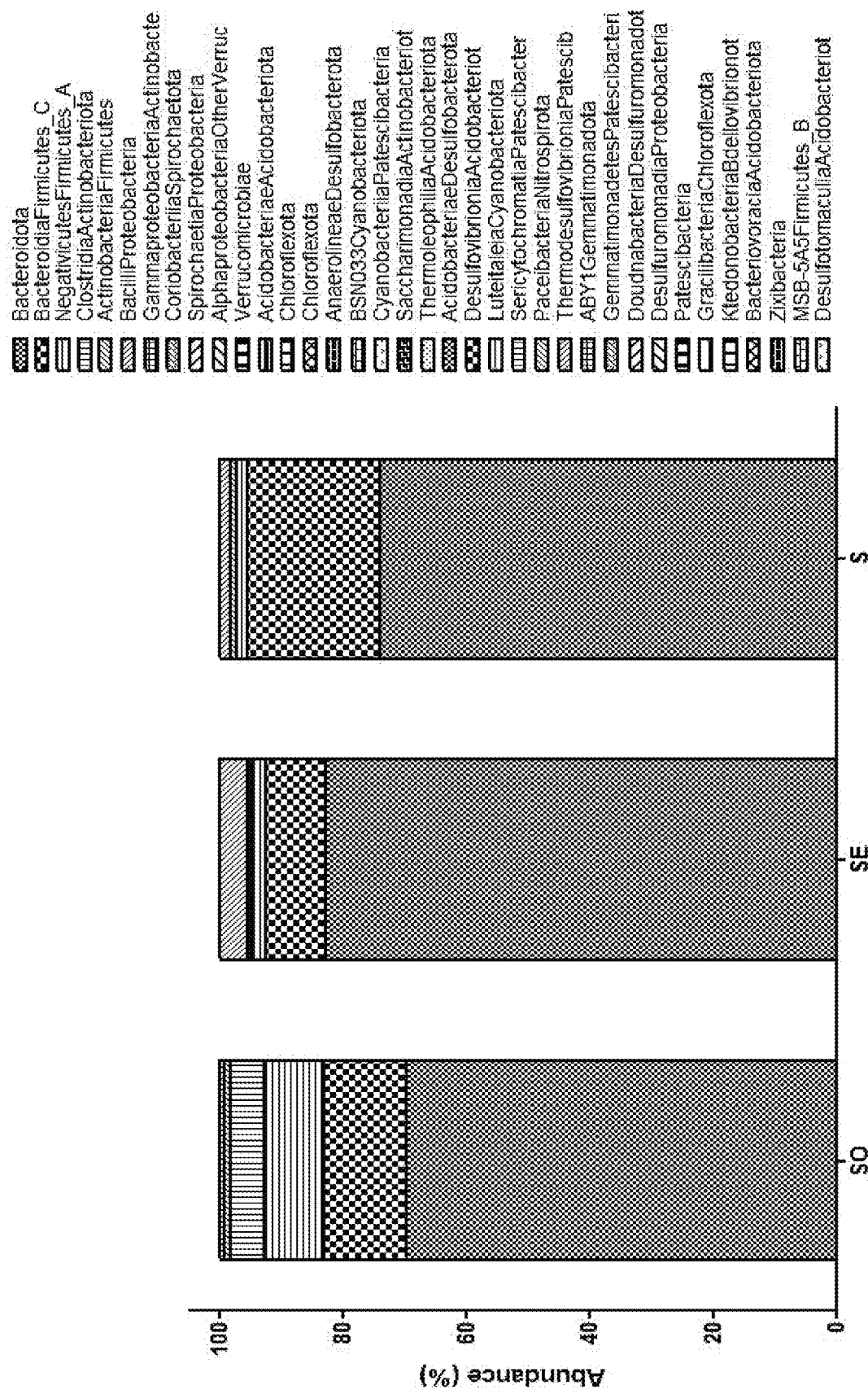
Figure 10B:

As a result, as illustrated in FIGS. 10A and 10B, the distribution of microflora for the sample control (SO) of human (female, 20 months old), test 1 (SE), and test 2 (S) was confirmed at class and genus levels. More specifically, as illustrated in FIG. 10A, the distribution of microflora at a class level was similar in control (SO) and test 1 (SE), and, as main classes, the class Bacteroidia (69.6%, 82.8%, 74%) of Bacteroidota, the class Negativicutes (13.4%, 9.6%, 21.5%) of Firmicutes, and the class *Clostridia* (9.7%, 2.0%, 1.8%) of Firmicutes were present.

As illustrated in FIG. 10B, it was also confirmed that there were big differences between the experimental groups at the genus level, and, as main genera, the genus *Bacteroides ovatus* (69.3%, 82.7%, 73.9%), the genus *Veillonella parvula* (13.1%, 8.8%, 19.7%), and the genus *Sutterella* sp3 (0.1%, 3.8%, 1.6%) were present.

For a sample control (YO) of human (female, 30 months old), test 1 (YE), and test 2 (Y), the distribution of intestinal microflora was analyzed at class and genus levels.

Figure 11A:
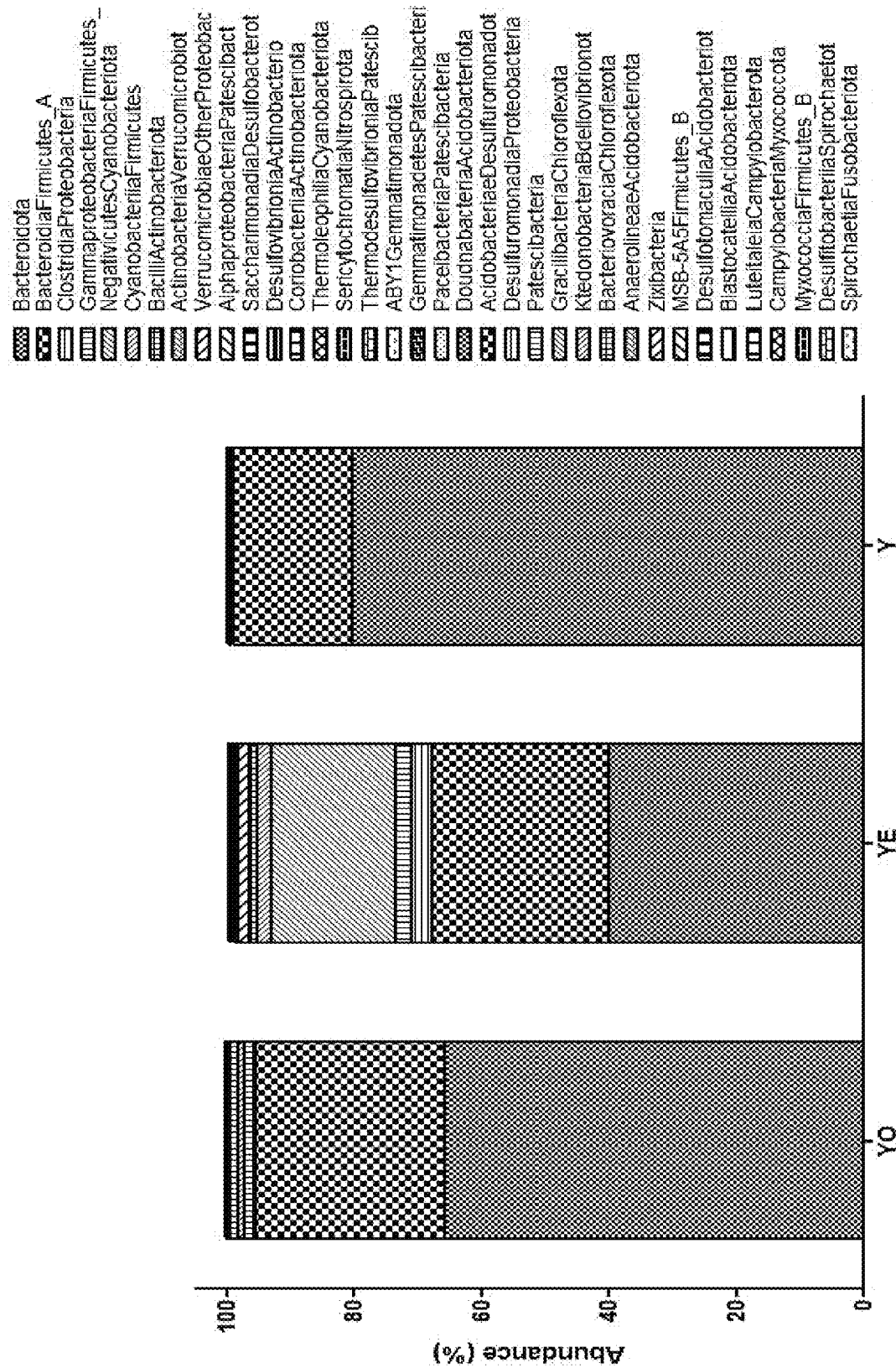
Figure 11B:
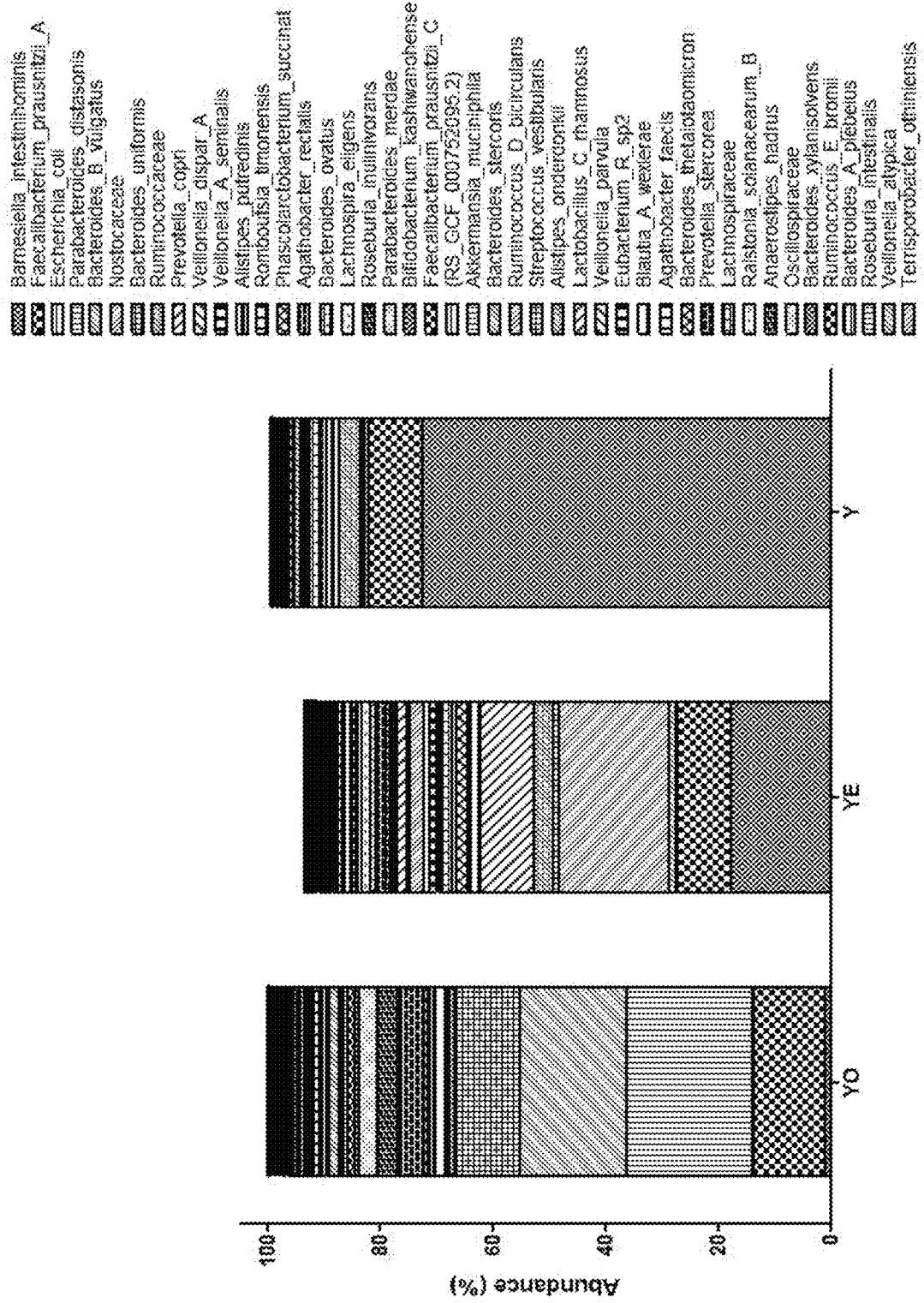

As a result, as illustrated in FIGS. 11A and 11B, the distribution of microflora for the sample control (SO) of human (female, 30 months old), test 1 (SE), and test 2 (S) was confirmed at class and genus levels. More specifically, as illustrated in FIG. 11A, the distribution of microflora at a class level was similar in control (YO) and test 1 (YE), and, as main classes, the class Bacteroidia (65.8%, 39.9%, 80.1%)) of Bacteroidota, the class *Clostridia* (29.7%, 27.8%, 18.8%) of Firmicutes, and the class Gammaproteobacteria (1.5%, 2.6%, 0.3%) of Proteobacteria were present.

In addition, as illustrated in FIG. 11B, very big differences between the experimental groups at the genus level were confirmed, and it was confirmed that, as main genera, the genus *Faecalibacterium prausnitzii* (12.8%, 9.5%, 9.4%), the genus *Barnesiella intestinihominis* (0.9%, 17.7%, 72.5%), and the genus *Parabacteroides distasonis* (22.5%, 0.3%, 0.1%) were present.

3-4. Confirmation of Similarity/Dissimilarity of Data for Intestinal Microflora in all Biological Groups and Experimental Groups A PCoA plot was performed using weighted normalized UniFrac values to explore the similarity/dissimilarity of data.

Figure 12:
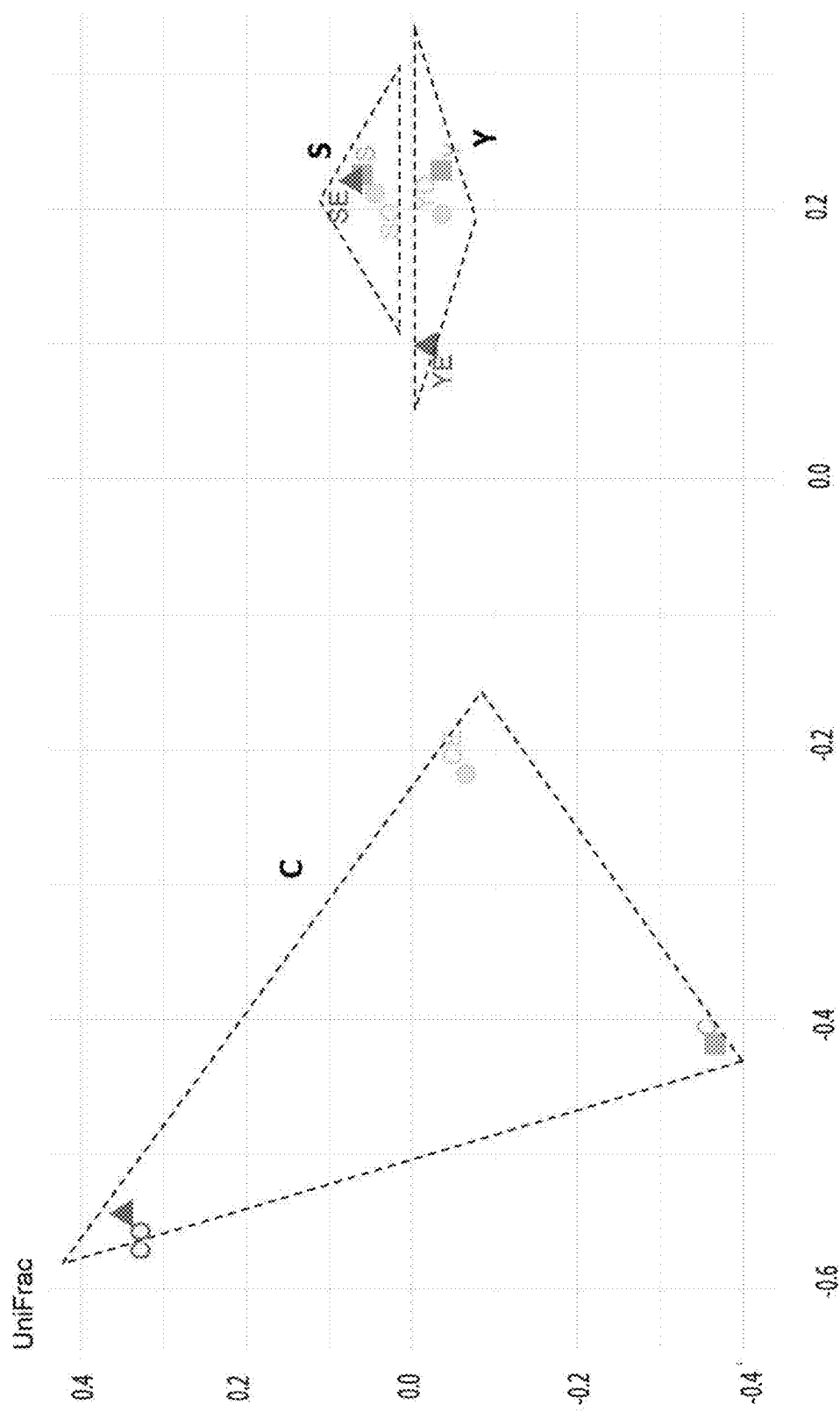
FIG. 12 illustrates PCoA plot results using weighted normalized UniFrac values to determine the similarity of a total of 9 pieces of data for each biological sample and experimental group.

As a result, as illustrated in FIG. 12, it was confirmed that the Canine-derived biological samples C were grouped apart from the human-derived biological samples Y and S and there were more distinct differences between the experimental groups (microwaves and the number of PCR cycles).

As illustrated in FIG. 12, it was also confirmed that, since CO and CE, SO and SE, and YO and Y are placed at similar positions, a control using a soil kit and two PCR cycles (Illumina NEXTERA XT kit) exhibited similar results to those of test 1 using microwaves and two PCR cycles (Illumina NEXTERA XT kit).

Based on the above results, it can be seen that a DNA extraction method using microwaves according to the present disclosure can be used in next generation sequencing (NGS) and it can be confirmed that the efficiency thereof is excellent.

As is apparent from the foregoing description, it was first verified that it is possible to construct a library for next generation sequencing using DNA extracted by applying microwaves to a biological sample, and thus a DNA extraction method using microwaves for next generation sequencing and merged primers, according to the present disclosure, reduce construction costs of the library and remarkably shorten construction time, and thus are expected to be usefully applied to the genetic analysis field and fields using the same.

The above description of the present disclosure is provided only for illustrative purposes, and it will be understood by one of ordinary skill in the art to which the present disclosure pertains that the disclosure may be embodied in various modified forms without departing from the spirit or essential characteristics thereof. Thus, the embodiments described herein should be considered in an illustrative sense only and not for the purpose of limitation.

What is claimed is:

1. A method for constructing a library for next generation sequencing (NGS), the method comprising the following processes:
   (1) preparing a mixture by mixing a human-derived biological sample with a buffer;
   (2) applying microwaves to the mixture for 30 seconds to 90 seconds;
   (3) recovering DNA;
   (4) amplifying a target DNA using primers, thereby providing an amplified product, and
   (5) purifying the amplified product and subjecting the purified product to library pooling, thereby forming the NGS library,
   wherein the human-derived biological sample has a concentration of 220 g/L to 280 g/L in the mixture and wherein the mixture has a volume of 20% to 32% with respect to the volume of a container containing the mixture, and wherein the biological sample of process (1) is selected from the group consisting of tissue, cells, blood, serum, saliva, a sample from a runny nose, genital mucus, and feces.

2. The method of claim 1, wherein process (3) comprises the following processes:
   (3-1) centrifuging the resulting mixture obtained in process (2); and
   (3-2) separating a supernatant from the centrifuged mixture obtained in process (3-1).

3. The method of claim 1, wherein the buffer of process (1) comprises a Tris-EDTA (TE) buffer.

4. The method of claim 1, wherein process (2) is repeatedly performed.

5. The method of claim 1, wherein the primers of process (4) comprise one or more primers selected from the group consisting of:
   a primer consisting of a nucleotide sequence represented by SEQ ID NO: 1;
   a primer consisting of a nucleotide sequence represented by SEQ ID NO: 2;
   a primer consisting of a nucleotide sequence represented by SEQ ID NO: 3;
   a primer consisting of a nucleotide sequence represented by SEQ ID NO: 4;
   a primer consisting of a nucleotide sequence represented by SEQ ID NO: 5;
   a primer consisting of a nucleotide sequence represented by SEQ ID NO: 6;
   a primer consisting of a nucleotide sequence represented by SEQ ID NO: 7;
   a primer consisting of a nucleotide sequence represented by SEQ ID NO: 8;
   a primer consisting of a nucleotide sequence represented by SEQ ID NO: 9;
   a primer consisting of a nucleotide sequence represented by SEQ ID NO: 10;
   a primer consisting of a nucleotide sequence represented by SEQ ID NO: 11;
   a primer consisting of a nucleotide sequence represented by SEQ ID NO: 12;
   a primer consisting of a nucleotide sequence represented by SEQ ID NO: 13;
   a primer consisting of a nucleotide sequence represented by SEQ ID NO: 14; and
   a primer consisting of a nucleotide sequence represented by SEQ ID NO: 15.

6. The method of claim 1, wherein the primers of process (4) consist of one or more primers selected from the group consisting of:
   a primer consisting of a nucleotide sequence represented by SEQ ID NO: 1;
   a primer consisting of a nucleotide sequence represented by SEQ ID NO: 2;
   a primer consisting of a nucleotide sequence represented by SEQ ID NO: 3;
   a primer consisting of a nucleotide sequence represented by SEQ ID NO: 4;
   a primer consisting of a nucleotide sequence represented by SEQ ID NO: 5;
   a primer consisting of a nucleotide sequence represented by SEQ ID NO: 6;
   a primer consisting of a nucleotide sequence represented by SEQ ID NO: 7;
   a primer consisting of a nucleotide sequence represented by SEQ ID NO: 8;
   a primer consisting of a nucleotide sequence represented by SEQ ID NO: 9;
   a primer consisting of a nucleotide sequence represented by SEQ ID NO: 10;
   a primer consisting of a nucleotide sequence represented by SEQ ID NO: 11;
   a primer consisting of a nucleotide sequence represented by SEQ ID NO: 12;
   a primer consisting of a nucleotide sequence represented by SEQ ID NO: 13;
   a primer consisting of a nucleotide sequence represented by SEQ ID NO: 14; and
   a primer consisting of a nucleotide sequence represented by SEQ ID NO: 15.

* * * * *